United States Patent
Kaita et al.

(10) Patent No.: US 8,653,290 B2
(45) Date of Patent: Feb. 18, 2014

(54) METALLOCENE COMPLEX AND POLYMERIZATION CATALYST COMPOSITION CONTAINING THE SAME

(75) Inventors: Shojiro Kaita, Wako (JP); Olivier Tardif, Wako (JP)

(73) Assignees: Riken, Saitama (JP); Bridgestone Corporation, Tokyo (JP); JSR Corporation, Tokyo (JP)

( * ) Notice: Subject to any disclaimer, the term of this patent is extended or adjusted under 35 U.S.C. 154(b) by 83 days.

(21) Appl. No.: 12/227,058

(22) PCT Filed: May 2, 2007

(86) PCT No.: PCT/JP2007/059389
§ 371 (c)(1),
(2), (4) Date: Nov. 6, 2008

(87) PCT Pub. No.: WO2007/129670
PCT Pub. Date: Nov. 15, 2007

(65) Prior Publication Data
US 2009/0264604 A1    Oct. 22, 2009

(30) Foreign Application Priority Data
May 9, 2006    (JP) ................. 2006-130550

(51) Int. Cl.
*C07F 17/00* (2006.01)
*C08F 4/52* (2006.01)

(52) U.S. Cl.
USPC ............... 556/1; 556/412; 502/155; 526/126; 526/160; 526/161; 526/943

(58) Field of Classification Search
USPC ............... 556/1, 412; 502/155; 526/160, 161, 526/943, 126
See application file for complete search history.

(56) References Cited

U.S. PATENT DOCUMENTS

| 5,066,741 | A | * | 11/1991 | Campbell, Jr. ................. | 526/171 |
| 5,252,766 | A | * | 10/1993 | Sakakura et al. ............. | 556/430 |
| 5,753,578 | A | * | 5/1998 | Santi et al. .................... | 502/114 |
| 2001/0018394 | A1 | * | 8/2001 | Brown ........................... | 502/102 |
| 2007/0232758 | A1 | | 10/2007 | Hou et al. | |

FOREIGN PATENT DOCUMENTS

| JP | 2004-27179 | 1/2004 |
| JP | 2007-063240 | 3/2007 |

OTHER PUBLICATIONS

Eppinger et al., "β-Si-H Agostic Rigidity in a Sovent-Free Indenyl0Derived ansa-Yttrocene Silylamide", Organometalloics, 1997, 16, p. 1813.*

H. J. Heeres et al., "Mono(pentamethylcyclopentadienyl) Complexes of Cerium(III). Synthesis, Molecular Structure, Thermal Stability, and Reactivity of $(C_5Me_5)CeX_2$ (X=2,6-Di-*tert*-butylphenoxo, $CH(SiMe_3)_2$, and $N(SiMe_3)_2$) Complexes", Organometallics, vol. 8, pp. 2637-2646, 1989.

M. Booji et al., "On the synthesis of monopentamethylcyclopentadienyl derivatives of yttrium, lanthanum, and cerium", Journal of Organometallic Chemistry, vol. 364, pp. 79-86, 1989.

T. D. Tilley et al., "Pentamethylcyclopentadienyl Derivatives of the Trivalent Lanthanide Elements Neodymium, Samarium, and Ytterbium", Inorg. Chem., vol. 20, pp. 3267-3270, 1981.

J. H. Yang et al., "New Binary Lanthanide Catalysts for Stereospecific Diene Polymerization", Macromolecules, vol. 15, pp. 230-233, 1982.

International Search Report issued Jul. 17, 2007 in the International (PCT) Application of which the present application is the U.S. National Stage.

E. Sheng et al., "A New Heteroatom Coordination Promoted Homolysis of Yb-N Bond. Synthesis and Structural Characterization of a New Class of Ytterbium(II) and Ytterbium(III) Complexes with Amido and Indenyl Ligands and Catalytic Activities of Ytterbium(II) Complexes", Organometallics, vol. 22, No. 4, pp. 684-692, 2003.

S. Kaita et al., "Butadiene Polymerization Catalyzed by Lanthanide Metallocene-Alkylaluminum Complexes with Cocatalysts: Metal-Dependent Control of 1,4-Cis/Trans Stereoselectivity and Molecular Weight", Macromolecules, vol. 39, pp. 1359-1363, 2006.

* cited by examiner

*Primary Examiner* — Caixia Lu
(74) *Attorney, Agent, or Firm* — Wenderoth, Lind & Ponack, L.L.P.

(57) ABSTRACT

Disclosed are a metallocene complex represented by the general formula (I), (II) or (III), and a polymerization catalyst composition containing such a metallocene complex. In the formulae (I), (II) and (III), M represents a lanthanoid element, scandium or yttrium; $Cp^R$ independently represents an unsubstituted or substituted indenyl; $Cp^{R'}$ represents an unsubstituted or substituted cyclopentadienyl, indenyl or fluorenyl; $R^a$-$R^f$ independently represents a hydrogen or an alkyl group having 1-3 carbon atoms; X and X' respectively represent a hydrogen atom, a halogen atom, an alkoxide group, a thiolate group, an amide group, a silyl group or a hydrocarbon group having 1-20 carbon atoms; L represents a neutral Lewis base; w represents an integer of 0-3; and [B]⁻ represents a non-coordinating anion.

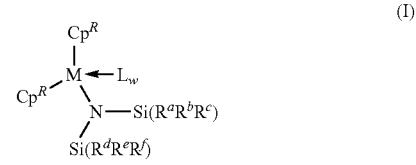

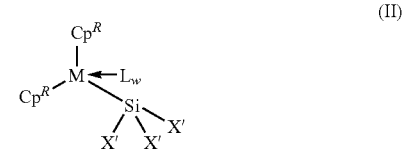

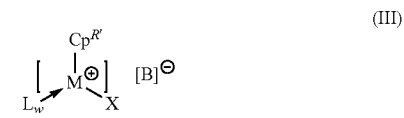

14 Claims, 12 Drawing Sheets

METALLOCENE COMPLEX AND POLYMERIZATION CATALYST COMPOSITION CONTAINING THE SAME

This application is a U.S. national stage of International Application No. PCT/JP2007/059389 filed May 2, 2007.

TECHNICAL FIELD

The present invention relates to a metallocene complex, a polymerization catalyst composition containing the metallocene complex, and a method of producing an addition polymer using the polymerization catalyst composition.

BACKGROUND ART

The metallocene complex is a compound used as one of catalyst components for various polymerization reactions, and a complex compound having one or more cyclopentadienyl groups or derivatives thereof each bound to the central metal. In particular, the metallocene complex having one cyclopentadienyl group or derivative thereof bound to the central metal is referred to as a half metallocene complex in some cases.

As the metallocene complex having gadolinium (Gd) as a central metal, there have been known bis(pentamethylcyclopentadienyl)gadolinium borate, dimethylaluminum (μ-dimethyl)bis(pentamethylcyclopentadienyl)gadolinium, and the like. It has been known that those metallocene complexes are used as components of polymerization catalyst compositions (for example, refer to Patent Document 1).

In addition, as a lanthanoid metallocene complex having a bis(trimethylsilyl)amide ligand, there have been known: one having cerium (Ce) as a central metal (refer to Non-Patent Document 1); one each having yttrium (Y), lanthanum (La), or cerium (Ce) as a central metal (refer to Non-Patent Document 2); and one having neodymium (Nd), samarium (Sm), or ytterbium (Yb) (refer to Non-Patent Document 3).

All of those lanthanoid metallocene complexes each having a bis(trimethylsilyl)amide ligand have a tetramethyl cyclopentadiene ligand.

On the other hand, there have conventionally been many proposals for the polymerization catalyst for conjugate diene polymerization.

For example, it has been known that high cis-1,4-bond conjugate diene polymers are obtained by using a composite catalyst system containing a neodymium compound and an organic aluminum compound as main components. Part of those polymers has been industrially used as a polymer catalyst system for butadiene (for example, refer to Non-Patent Documents 4 and 5).

In addition, it has been reported that the high cis-1,4-bond conjugate diene polymer can be obtained by using a catalyst system containing the above dimethylaluminum (μ-dimethyl)bis(cyclopentadienyl) gadolinium and the like (refer to Patent Document 1).

However, there has been demanded a method of producing effectively a conjugate diene polymer having a high content of cis-1,4-structures in a micro structure, a high molecular weight, and a sharp molecular weight distribution, and hence development of a polymerization catalyst therefor has been demanded.

Patent Document 1: JP 2004-27179 A
Non-Patent Document 1: Organometallics, 1989, 8, 2637-2646
Non-Patent Document 2: Journal of Organometallic Chemistry, 364 (1989) 79-86.
Non-Patent Document 3: Inorg. Chem. 1981, 20, 3267-3270
Non-Patent Document 4: Macromolecules, 15, 230, 1982.
Non-Patent Document 5: Makromol. Chem., 94, 119, 1981.

DISCLOSURE OF THE INVENTION

An object of the present invention is to provide a novel metallocene complex and a novel polymerization catalyst reaction for a conjugate diene, a monoolefin, and the like using the metallocene complex.

The inventor of the present invention has extensively studied, and accomplished the invention described below.

That is, the present invention is as follows.

[1] A metallocene complex represented by the following general formula (I),

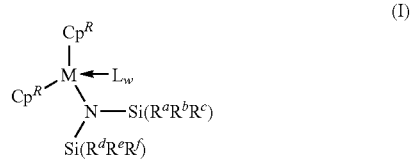

where: M represents a lanthanoid element, scandium, or yttrium;
$Cp^R$ independently represents an unsubstituted or substituted indenyl group;
$R^a$ to $R^f$ independently represents hydrogen or an alkyl group having 1 to 3 carbon atoms;
L represents a neutral Lewis base; and
w represents an integer of 0 to 3.

[2] A metallocene complex represented by the following general formula (II),

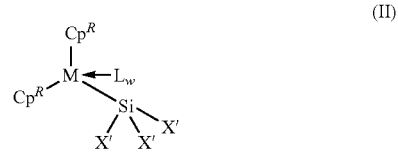

where: M represents a lanthanoid element, scandium, or yttrium;
$Cp^R$ independently represents an unsubstituted or substituted indenyl group;
X' represents a hydrogen atom, a halogen atom, an alkoxide group, a thiolate group, an amide group, a silyl group, or a hydrocarbon group having 1 to 20 carbon atoms;
L represents a neutral Lewis base; and
w represents an integer of 0 to 3.

[3] A half metallocene cation complex represented by the following general formula (III),

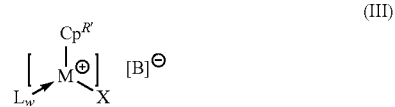

where: M represents a lanthanoid element, scandium, or yttrium;

$Cp^{R'}$ represents an unsubstituted or substituted cyclopentadienyl, indenyl, or fluorenyl group;

X represents a hydrogen atom, a halogen atom, an alkoxide group, a thiolate group, an amide group, a silyl group, or a hydrocarbon group having 1 to 20 carbon atoms;

L represents a neutral Lewis base;

w represents an integer of 0 to 3; and $[B]^-$ represents a non-coordinating anion.

[4] The half metallocene cation complex according to [3], wherein $Cp^{R'}$ represents an unsubstituted or substituted indenyl group.

[5] A polymerization catalyst composition, comprising at least one kind of complex selected from the group consisting of the metallocene complexes according to [1] and [2] and the half metallocene cation complex according to [3] and [4].

[6] The polymerization catalyst composition according to [5], which is used for polymerizing a conjugate diene.

[7] The polymerization catalyst composition according to [5] or [6], further comprising an aluminoxane.

[8] The polymerization catalyst composition according to any one of [5] to [7], further comprising one of or both an organic aluminum compound and an ionic compound.

[9] A method of producing an addition polymer, comprising polymerizing addition-polymerizable monomers in the presence of the polymerization catalyst composition according to any one of [5] to [8].

[10] The method according to [9], wherein:
the addition-polymerizable monomer is a conjugate diene; and
the addition polymer is a conjugate diene polymer.

[11] The method according to [9], wherein:
the addition-polymerizable monomer is 1,3-butadiene; and
the addition polymer is a butadiene polymer.

[12] The method according to [9], wherein:
the addition-polymerizable monomer is a disconjugate olefin; and
the addition polymer is a disconjugate olefin polymer.

[13] The method according to [9], wherein:
the addition-polymerizable monomer is at least one monoolefin selected from C2 to C10 disconjugate olefins and a styrene; and
the addition polymer is a monoolefin polymer or copolymer each obtained by reacting at least one selected from C2 to C10 disconjugate olefins with styrene.

[14] The method according to [13], wherein:
the addition-polymerizable monomer further comprises a conjugate diene; and
the addition polymer is a copolymer of the conjugate diene and the monoolefin.

[15] A method for producing a half metallocene cation complex represented by the following general formula (III), comprising subjecting a compound represented by the following general formula (IV) to a reaction with an ionic compound represented by the general formula $[A]^+[B]^-$

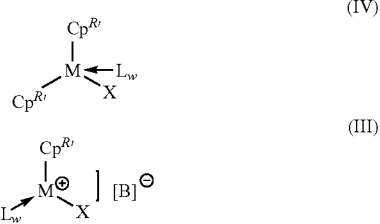

where: M represents a lanthanoid element, scandium, or yttrium;

$Cp^{R'}$ independently represents an unsubstituted or substituted cyclopentadienyl, indenyl, or fluorenyl group;

X represents a hydrogen atom, a halogen atom, an alkoxide group, a thiolate group, an amide group, a silyl group, or a hydrocarbon group having 1 to 20 carbon atoms;

L represents a neutral Lewis base;

w represents an integer of 0 to 3;

$[A]^+$ represents a cation; and $[B]^-$ represents a non-coordinating anion.

[16] The method according to [15], wherein $Cp^{R'}$ represents an unsubstituted or substituted indenyl group.

DESCRIPTION OF THE PREFERRED EMBODIMENTS

<Metallocene Complex of the Present Invention>

Figure 1:
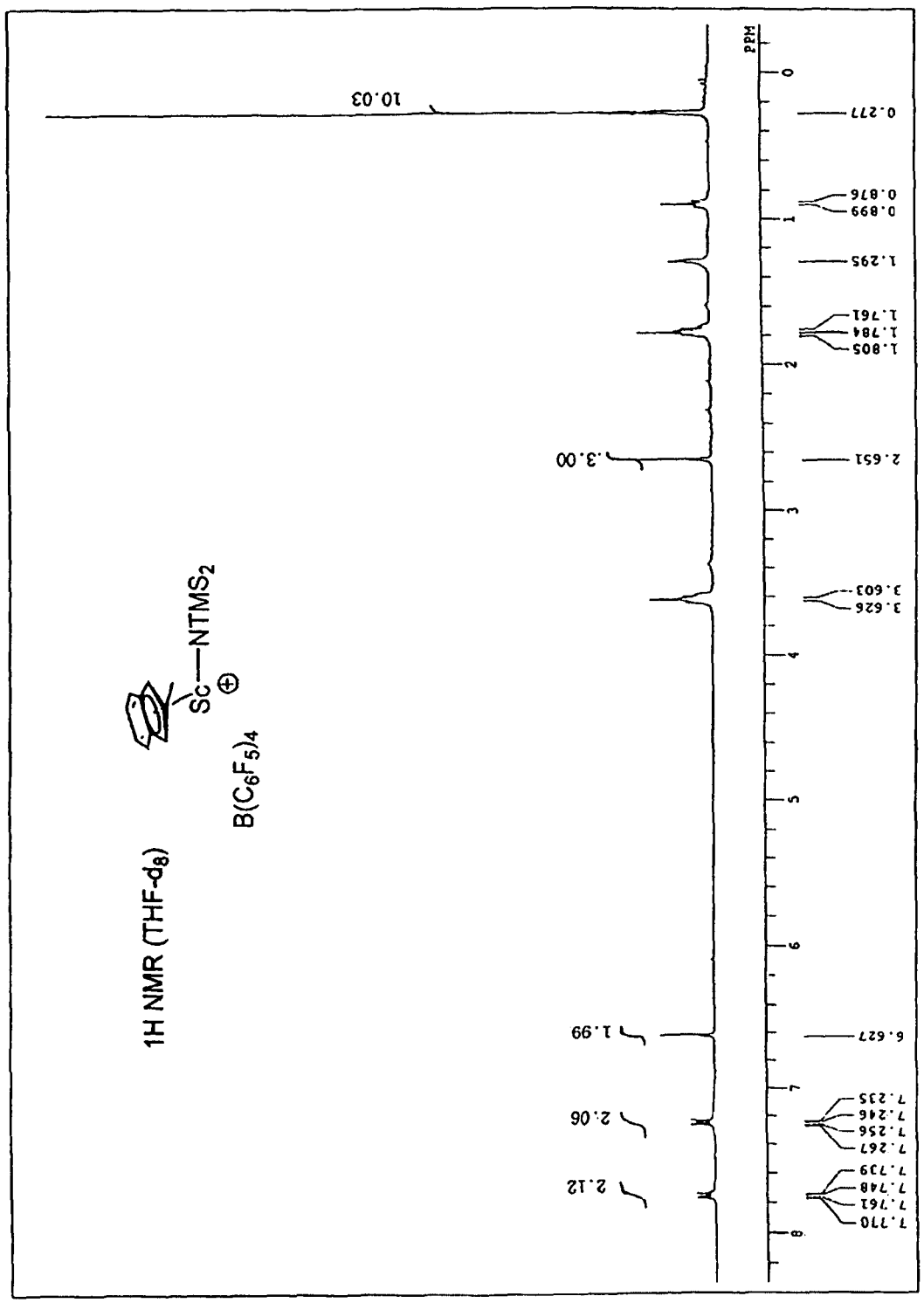
FIG. 1 is an $^1$H-NMR spectrum chart of $[(2-MeC_9H_6)ScN(SiMe_3)_2(THF)_2][B(C_6F_5)_4]$.

A metallocene complex of the present invention is represented by the following general formula (I) or (II).

The metallocene complex represented by the general formula (I) comprises a lanthanoid element, scandium, or yttrium as a central metal represented by M, two indenyl or substituted indenyl groups represented by $cp^R$, and one bis(trialkylsilyl)amide ligand represented by $[-N(SiR_3)_2]$.

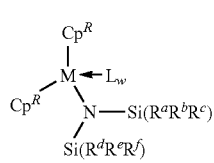
(I)

The metallocene complex represented by the general formula (II) comprises a lanthanoid element, scandium, or yttrium as a central metal represented by M, two indenyl or substituted indenyl groups represented by $Cp^R$, and one silyl ligand represented by [—$SiX'_3$].

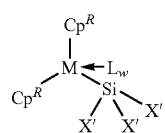
(II)

<Half Metallocene Cation Complex of the Present Invention>

The half metallocene cation complex of the present invention is represented by the following formula (III) and comprises M which represents a lanthanoid element, scandium, or yttrium as a central metal, $Cp^{R'}$ which represents one substituted or unsubstituted cyclopentadienyl, indenyl, or fluorenyl group, X selected from the group consisting of hydrogen atom, halogen atom, alkoxide group, thiolate group, amide group, silyl group, and hydrocarbon group having 1 to 20 carbon atoms, and [B]⁻ which represents a non-coordinating anion.

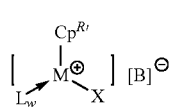
(III)

$Cp^R$ in the general formulae (I) and (II) each represents an unsubstituted or substituted indenyl group. $Cp^R$ having an indenyl ring as a base skeleton may be represented by $C_9H_{7-x}R_x$ or $C_9H_{11-x}R_x$. Here, x represents an integer of 0 to 7 or 0 to 11, respectively.

R independently preferably represents a hydrocarbyl group or a metalloid group.

The hydrocarbyl group has preferably 1 to 20 carbon atoms, more preferably 1 to 10 carbon atoms, and still more preferably 1 to 8 carbon atoms. In addition, preferable specific examples of the hydrocarbyl group include a methyl group, an ethyl group, a phenyl group, and a benzyl group.

Examples of metalloid in the metalloid group include germyl (Ge), stannyl (Sn), and silyl (Si). In addition, the metalloid group has preferably a hydrocarbyl group which is as described above. Specific examples of the metalloid group include a trimethyl silyl group.

Examples of the substituted indenyl group specifically include 2-phenyl indenyl, 2-methyl indenyl, and 1-methyl-2-phenyl indenyl group.

Two CPR in the general formulae (I) and (II) are the same as or different from each other.

CPR in the general formula (III) represents a substituted or unsubstituted cyclopentadienyl, indenyl, or fluorenyl group. $Cp^{R'}$ preferably represents a substituted or unsubstituted indenyl group.

$Cp^{R'}$ having a cyclopentadienyl ring as a base skeleton is represented by $C_5H_{5-x}R_x$. Here, x represents an integer of 0 to 5. R independently preferably represents a hydrocarbyl group or a metalloid group. The hydrocarbyl group has preferably 1 to 20 carbon atoms, more preferably 1 to 10 carbon atoms, and still more preferably 1 to 8 carbon atoms. In addition, preferable specific examples of the hydrocarbyl group include a methyl group, an ethyl group, a propyl group, a phenyl group, and a benzyl group. Examples of metalloid in the metalloid group include germyl (Ge), stannyl (Sn), and silyl (Si). In addition, the metalloid group has preferably a hydrocarbyl group which is as described above. Specific examples of the metalloid group include a trimethyl silyl group.

As $Cp^{R'}$ having a cyclopentadienyl ring as a base skeleton, the followings are specifically exemplified:

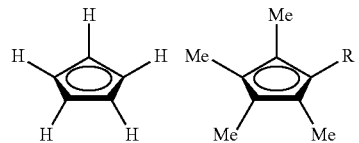

where R represents a hydrogen atom, a methyl group, or an ethyl group.

$Cp^{R'}$ having an indenyl ring as a base skeleton is defined as the same as $Cp^R$ in the general formula (I) and preferable examples thereof are also the same as those of $Cp^R$ in the general formula (I).

$Cp^{R'}$ having a fluorenyl ring as a base skeleton may be represented by $C_{13}H_{9-x}R_x$ or $C_{13}H_{17-x}R_x$. Here, x represents an integer of 0 to 9 or 0 to 17, respectively. R independently represents a hydrocarbyl group or a metalloid group. The hydrocarbyl group has preferably 1 to 20 carbon atoms, more preferably 1 to 10 carbon atoms, and still more preferably 1 to 8 carbon atoms. In addition, preferable specific examples of the hydrocarbyl group include a methyl group, an ethyl group, a phenyl group, and a benzyl group. Examples of metalloid in the metalloid group include germyl (Ge), stannyl (Sn), and silyl (Si). In addition, the metalloid group has preferably a hydrocarbyl group which is as described above. Specific examples of the metalloid group include a trimethyl silyl group.

The central metal represented by M in the general formulae (I), (II), and (III) represents a lanthanoid element, scandium, or yttrium. The lanthanoid elements include 15 elements with atomic numbers 57 to 71, and may be any one of them. Preferable examples of the central metal represented by M include samarium (Sm), neodymium (Nd), praseodymium (Pr), gadolinium (Gd), terbium (Tb), cerium (Ce), holmium (Ho), scandium (Sc), and yttrium (Y).

The metallocene complex of the present invention represented by the general formula (I) includes a bistrialkyl silyl amide ligand represented by [—$N(SiR_3)_2$]. Alkyl groups represented by R ($R^a$ to $R^f$ in the general formula (I)) in the bistrialkyl silyl amide independently represents hydrogen or an alkyl group having 1 to 3 carbon atoms, and it is preferred that at least one of $R^a$, $R^b$, and $R^c$ represent an alkyl group having 1 to 3 carbon atoms and at least one of $R^d$, $R^e$, and $R^f$ represent an alkyl group having 1 to 3 carbon atoms. It is preferred that two or more of $R^a$, $R^b$, and $R^c$ represent alkyl groups each having 1 to 3 carbon atoms and two or more of $R^d$, $R^e$, and $R^f$ represent alkyl groups each having 1 to 3 carbon atoms. Here, as the alkyl group having 1 to 3 carbon atoms, methyl is preferred.

The metallocene complex of the present invention represented by the general formula (II) include a silyl ligand represented by [—SiX'₃]. X' in the silyl ligand represented by [—SiX'₃] is a group defined as the same as X in the general formula (III) described below and preferable examples are also the same as those of X in the general formula (III).

In the general formula (III), X represents a group selected from a hydrogen atom, halogenatoms, alkoxide groups, thiolate groups, amide groups, and hydrocarbon groups each having 1 to 20 carbon atoms.

In the general formula (III), the alkoxide group represented by X may be any one of aliphatic alkoxy groups such as a methoxy group, an ethoxy group, a propoxy group, an n-butoxy group, an isobutoxy group, a sec-butoxy group, and a tert-butoxy group, and aryl oxide groups such as a phenoxy group, a 2,6-di-tert-butylphenoxy group, a 2,6-diisopropylphenoxy group, a 2,6-dineopentylphenoxy group, a 2-tert-butyl-6-isopropylphenoxy group, a 2-tert-butyl-6-neopentylphenoxy group, and a 2-isopropyl-6-neopentylphenoxy group. The 2,6-di-tert-butylphenoxy group is preferred.

In the general formula (III), the thiolate group represented by X may be any one of aliphatic thiolate groups such as a thiomethoxy group, a thioethoxy group, a thiopropoxy group, a thio-n-butoxy group, a thioisobutoxy group, a thio-sec-butoxy group, and a thio-tert-butoxy group, and aryl thiolate groups such as a thiophenoxy group, a 2,6-di-tert-butylthiophenoxy group, a 2,6-diisopropylthiophenoxy group, a 2,6-dineopentylthiophenoxy group, a 2-tert-butyl-6-isopropylthiophenoxy group, a 2-tert-butyl-6-thioneopentylphenoxy group, a 2-isopropyl-6-thioneopentylphenoxy group, and a 2,4,6-triisopropylthiophenoxy group. The 2,4,6-triisopropylthiophenoxy group is preferred.

In the general formula (III), the amide group represented by X may be any one of aliphatic amide groups such as a dimethyl amide group, a diethyl amide group, and a diisopropyl amide group, arylamide groups such as a phenyl amide group, a 2,6-di-tert-butylphenyl amide group, a 2,6-diisopropylphenyl amide group, a 2,6-dineopentylphenyl amide group, a 2-tert-butyl-6-isopropylphenyl amide group, a 2-tert-butyl-6-neopentylphenyl amide group, a 2-isopropyl-6-neopentylphenyl amide group, and a 2,4,6-tert-butylphenyl amide group, and bistrialkylsilyl amide groups such as a bistrimethylsilyl amide group. The bistrimethylsilyl amide group is preferred.

In the general formula (III), the silyl group represented by X may be any one of a trimethylsilyl group, a tris(trimethylsilyl) silyl group, a bis(trimethylsilyl)methylsilyl group, a trimethylsilyl(dimethyl)silyl group, and a triisopropylsilyl (bistrimethylsilyl)silyl group. The tris(trimethylsilyl)silyl group is preferred.

In the general formula (III), the halogen atom represented by X may be any one of a fluorine atom, a chlorine atom, a bromine atom, and an iodine atom. The chlorine atom and the iodine atom are preferred. Specific examples of the hydrocarbon group having 1 to 20 carbon atoms include: linear or branched aliphatic hydrocarbon groups such as a methyl group, an ethyl group, an n-propyl group, an isopropyl group, an n-butyl group, an isobutyl group, a sec-butyl group, a tert-butyl group, a neopentyl group, a hexyl group, and an octyl group; aromatic hydrocarbon groups such as a phenyl group, a tolyl group, and a naphthyl group; aralkyl groups such as a benzyl group; and hydrocarbon groups such as a trimethylsilylmethyl group and a bistrimethylsilylmethyl group each containing a silicon atom. Of those, the methyl group, the ethyl group, the isobutyl group, the trimethylsilylmethyl group, and the like are preferred. The bistrimethylsilylamide group and the hydrocarbon group having 1 to 20 carbon atoms are preferred as X.

In the general formula (III), examples of the non-coordinating anion represented by [B]⁻ include tetravalent boron anions. Examples of the tetravalent boron anion include tetraphenyl borate, tetrakis(monofluorophenyl)borate, tetrakis (difluorophenyl)borate, tetrakis(trifluorophenyl)borate, tetrakis(tetrafluorophenyl)borate, tetrakis(pentafluorophenyl) borate, tetrakis(tetrafluoromethylphenyl)borate, tetra(tolyl) borate, tetra(xylyl)borate, (tripheyl, pentafluorophenyl) borate, [tris(pentafluorophenyl), phenyl]borate, and tridecahydride-7,8-dicarbaundecaborate. The tetrakis(pentafluorophenyl)borate is preferably exemplified.

The metallocene complexes and the half metallocene cation complex of the present invention may include 0 to 3 (preferably 0 or 1) neutral Lewis bases represented by L. Examples of the neutral Lewis base include tetrahydrofuran, diethyl ether, dimethyl aniline, trimethyl phosphine, lithium chloride, neutral olefins, and neutral diolefins. When a plurality of neutral Lewis bases represented by L are incorporated, respective L may be the same as or different from each other.

The metallocene complexes and the half metallocene cation complex of the present invention may be each present as a monomer as represented by the general formulae (I) to (III), or as a dimer or a multimer having two or more monomers.

The metallocene complex represented by the general formula (I) of the present invention is produced by the following procedure, for example.

The complex represented by the general formula (I) can be obtained by subjecting a lanthanoid trishalide, a scandium trishalide, or a yttrium trishalide to react in a solvent with a salt of indenyl (for example, a potassium salt or a lithium salt) and a salt of bis(trialkylsilyl)amide (for example, a potassium salt or a lithium salt).

The complex may be produced in mild conditions because reaction temperature has only to be set to about room temperature. In addition, reaction time is arbitrary, but about several hours to several tens of hours. A reaction solvent is not particularly limited, and a solvent that solves a raw material and a product is preferred. For example, toluene may be used.

Hereinafter, a reaction example for obtaining the complex represented by the general formula (I) is described.

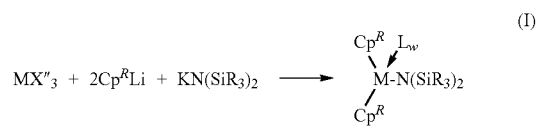

(I)

where X" represents a halide.

The metallocene complex represented by the general formula (II) of the present invention is produced by the following procedure, for example.

The complex represented by the general formula (II) can be obtained by subjecting a lanthanoid trishalide, a scandium trishalide, or a yttrium trishalide to react in a solvent with a salt of indenyl (for example, a potassium salt or a lithium salt) and a salt of silyl (for example, a potassium salt or a lithium salt).

The complex may be produced in mild conditions because reaction temperature has only to be set to about room temperature. In addition, reaction time is arbitrary, but about several hours to several tens of hours. A reaction solvent is not particularly limited, and a solvent that solves a raw material and a product is preferred. For example, toluene may be used.

Hereinafter, a reaction example for obtaining the complex represented by the general formula (II) is described.

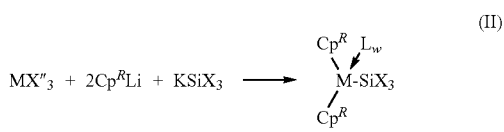

where X" represents a halide.

The complex represented by the general formula (III) is obtained by the following reaction, for example:

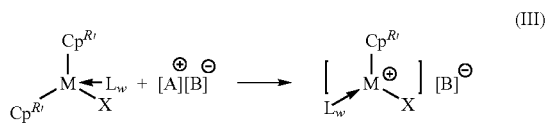

where: M represents a lanthanoid element, scandium, or yttrium;

$Cp^{R'}$ independently represents an unsubstituted or substituted cyclopentadienyl, indenyl, or fluorenyl;

X represents a hydrogen atom, a halogen atom, an alkoxide group, a thiolate group, an amide group, a silyl group, or a hydrocarbon group having 1 to 20 carbon atoms;

L represents a neutral Lewis base;

w represents an integer of 0 to 3;

[A]$^+$ represents a cation; and

[B]$^-$ represents a non-coordinating anion.

Examples of the cation represented by [A]$^+$ include a carbonium cation, an oxonium cation, an amine cation, a phosphonium cation, a cycloheptatrienyl cation, and a ferrocenium cation containing a transition metal.

Examples of the carbonium cation include trisubstituted carbonium cations such as a triphenylcarbonium cation and a tri(substituted phenyl)carbonium cation. Specific examples of the trisubstituted phenylcarbonium cation include a tri(methylphenyl)carbonium cation.

Examples of the amine cation include: trialkylammonium cations such as a trimethylammonium cation, a triethylammonium cation, a tripropylammonium cation, and a tributylammonium cation; N,N-dialkylanilinium cations such as an N,N-dimethylammonium cation, N,N-diethylammonium cation, and an N,N-2,4,6-pentamethylammonium cation; and dialkylammonium cations such as a diisopropylammonium cation and a dicyclohexylammonium cation.

Examples of the phosphonium cation include triarylphosphonium cations such as a triphenylphosphonium cation, a tri(methylphenyl)phosphonium cation, and a tri(dimethylphenyl)phosphonium cation.

Of those cations, the anilinium cations or the carbonium cations are preferred and the anilinium cations are particularly preferred.

The ionic compound represented by the general formula [A]$^+$[B]$^-$ and used in the above reaction is one which is obtained by combining any one selected from the non-coordinating anions described above and any one selected from the cations described above.

Preferable examples of the ionic compound include N,N-dimethylanilinium tetrakis(pentafluorophenyl)borate and triphenylcarbonium tetrakis(pentafluorophenyl)borate.

The ionic compound represented by the general formula [A]$^+$[B]$^-$ is added in an amount of preferably 0.1 to 10-fold mol and more preferably about 1-fold mol with respect to the metallocene complex.

When the half metallocene cation complex represented by the general formula (III) is used in polymerization reaction, the half metallocene cation complex represented by the general formula (III) as it is may be provided in the polymerization reaction system, or alternatively, the compound represented by the general formula (IV) and the ionic compound represented by the general formula [A]$^+$[B]$^-$ may be separately provided in the polymerization reaction system, whereby the half metallocene cation complex represented by the general formula (III) is formed in the reaction system.

In addition, the half metallocene cation complex represented by the general formula (III) may be formed in the reaction system by using the metallocene complex represented by the general formula (I) or (II) and the ionic compound represented by the general formula [A]$^+$[B]$^-$ in combination.

Structures of the metallocene complex and the half metallocene cation complex of the present invention represented by the general formula (I), (II), or (III) can be determined preferably by X-ray crystallography.

FIGS. 4 to 14 are ORTEP drawings showing results of the X-ray crystallography of respective metallocene complexes and half metallocene cation complex.

The metallocene complexes and the half metallocene cation complex of the present invention may be applied to various fields, and each may be used as a component for a polymerization catalyst composition, for example.

<Polymerization Catalyst Composition of the Present Invention>

The polymerization catalyst composition of the present invention comprises the metallocene complex or/and the half metallocene cation complex. Preferably, the polymerization catalyst composition further comprises another component such as a co-catalyst, which is contained in the general polymerization catalyst composition containing a metallocene complex.

The co-catalyst may be arbitrarily selected from components used as the co-catalyst for the general polymerization catalyst composition containing a metallocene complex. Preferable examples of the co-catalyst include aluminoxanes, organic aluminum compounds and the above ionic compounds. One kind or plural kinds of them may be contained in the polymerization catalyst composition of the present invention.

The aluminoxane is preferably an alkyl aluminoxane. Examples of the alkyl aluminoxane include methyl aluminoxane (MAO) and modified methyl aluminoxanes. In addition, preferable examples of the modified methyl aluminoxane include MMAO-3A (manufactured by Tosoh Finechem Corporation).

A content of the aluminoxane in the polymerization catalyst composition of the present invention is preferably about 10 to 1,000 (more preferably about 100) at an element ratio (Al/M) of the aluminum element Al of the aluminoxane to the central metal element M in the metallocene complex.

On the other hand, examples of the organic aluminum compound include trialkyl aluminum, dialkyl aluminum chloride, alkyl aluminum dichloride, and dialkyl aluminum halide. Preferred is the trialkyl aluminum. Examples of the trialkyl aluminum include triethyl aluminum and triisobutyl aluminum.

A content of the organic aluminum compound in the polymerization catalyst composition of the present invention is preferably 1 to 50-fold mol and more preferably about 10-fold mol with respect to the metallocene complex.

The polymerization catalyst composition of the present invention is provided in a polymerization reaction system of arbitrary monomer having addition polymerizability. For example, 1) a composition containing respective constituent components (such as the metallocene complex and the co-catalyst) may be provided in the polymerization reaction system or 2) respective constituent components may be separately provided in the polymerization reaction system, to thereby give a composition in the reaction system.

In the above item 1), the phrase "a composition is provided" includes that a metallocene complex activated by the co-catalyst (activated species) is provided.

Examples of the monomers polymerized by using the polymerization catalyst composition of the present invention include olefin-based monomers, epoxy-based monomers, isocyanate-based monomers, lactone-based monomers, lactide-based monomers, cyclic carbonate-based monomers, and alkyne-based monomers.

Examples of the olefin-based monomer include conjugate olefins and disconjugate olefins. Specific examples thereof include monoolefins of α-olefins and dienes such as styrene, α-methyl styrene, ethylene, and propylene.

Further, examples of the diene include conjugate dienes such as 1,3-butadiene, isoprene, 1,3-pentadiene, 2-ethyl-1,3-butadiene, 2,3-dimethyl butadiene, 2-methyl pentadiene, 4-methyl pentadiene, and 2,4-hexadiene. More preferable conjugate diene is 1,3-butadiene and isoprene.

The metallocene complex and the half metallocene cation complex (represented by the general formula (I), (II), or (III)) contained in the catalyst composition of the present invention are selected in accordance with intended use of the catalyst. For example, when the catalyst is used as a catalyst for a conjugate diene polymerization, 1) a catalyst activity can be increased and 2) a cis-content of the obtained polydiene can be increased by using a metallocene complex having a lanthanoid element, scandium, or yttrium as a central metal represented by M.

In addition, when the catalyst is used as the catalyst for a conjugate diene polymerization, 1) the catalyst activity and 2) the cis-1,4-content of the obtained polydiene can be controlled by adjusting the steric size of the substituent on $Cp^R$. That is, by sterically reducing the size of the substituent on $Cp^R$ (for example, an unsubstituted indenyl is adapted as $Cp^R$), the cis-1,4 content of the obtained polydiene can be made high. On the other hand, by sterically enlarging the size of the substituent on $Cp^R$ (for example, tetramethylethyl indenyl is adapted as $Cp^R$), the polydiene can be obtained at a good yield with a short time reaction.

Further, when the catalyst is used as the catalyst for a conjugate diene polymerization, 1) the catalyst activity of the polymerization catalyst composition can be adjusted and 2) a cis-content of the obtained polydiene can be increased by combining the metallocene complex and half metallocene cation complex represented by the general formula (I), (II), or (III) with an appropriate co-catalyst. Hereinafter, respective relationships between the metallocene complexes contained in the catalyst composition, each of which is represented by the general formula (I), (II), or (III), and the co-catalyst are described.

<Catalyst Composition Containing Metallocene Complex Represented by General Formula (I) or (II)>

When the metallocene complex represented by the general formula (I) or (II) is used as a component of the catalyst composition for a conjugate diene polymerization, a number average molecular weight of the polydiene to be obtained is liable to be high by using an aluminoxane as a co-catalyst.

<Catalyst Composition Containing Half Metallocene Cation Complex Represented by General Formula (III)>

By combining preferably with an organic aluminum compound, the half metallocene cation complex represented by the general formula (III) can be used effectively for polymerizations of C2 to C10 disconjugate olefins such as ethylene or propylene and monoolefins such as styrene.

The polymerization catalyst composition of the present invention is used as a polymerization catalyst composition in not only a homopolymerization reaction but also in a copolymerization reaction. As a copolymer obtained by the copolymerization reaction, a copolymer of two or more kinds of monoolefin monomers and a copolymer of a monoolefin and a conjugate diene are exemplified.

<Method of Producing Addition Polymer of the Present Invention>

The method of producing an addition polymer of the present invention comprises subjecting an arbitrary monomer having addition polymerizability to an addition polymerization in the presence of the catalyst composition. The production method of the present invention may be the same as a conventional method of producing an addition polymer by an addition polymerization reaction using a coordinated ionic polymerization catalyst except that the catalyst composition of the present invention is used as a polymerization catalyst. That is, the method of producing an addition polymer of the present invention may employ any one of arbitrary methods such as a solution polymerization, a suspension polymerization, a liquid-phase block polymerization, an emulsion polymerization, a gas-phase polymerization, and a solid-phase polymerization.

When the solution polymerization is employed, the solvent to be used is not particularly limited as long as the solvent is inactive in the polymerization reaction and solves the monomer for polymerization and the catalyst composition. An amount of the solvent to be used is arbitrary, and such an amount that the concentration of the complex contained in the polymerization catalyst is 0.1 to 0.0001 mol/l is preferred.

In the method of producing an addition polymer of the present invention, an amount of the catalyst composition with respect to the amount of the monomer may be set to the same as that of the general catalyst composition containing an metallocene complex.

According to the method of producing an addition polymer of the present invention, random copolymers, alternating copolymers, block copolymers, and other high-sequenced copolymers as well as homopolymers can be produced.

Hereinafter, examples of procedures for producing polybutadiene from 1,3-butadiene by the production method of the present invention are described.

(1) The metallocene complex of the present invention and if necessary a co-catalyst are added to a solvent. Here, the metallocene complex may be changed to an activated form. 1,3-butadiene is added thereto, whereby polybutadiene is obtained.

(2) Constituent components of the catalyst composition are separately added to a solvent containing 1,3-butadiene or an activated catalyst composition previously prepared is added to the solvent containing 1,3-butadiene, whereby polybutadiene is obtained.

Both procedures are conducted preferably under an atmosphere of inert gas. Examples of the inert gas include a nitrogen gas and an argon gas.

In the production of butadiene, the metallocene complex in a concentration of about 1/10,000 to 1/1,000-fold mol with respect to 1,3-butadiene is preferably used.

A temperature in the polymerization reaction is not particularly limited and may be in a range of −100° C. to 200° C. or may be set to about room temperature. If the reaction temperature is increased, a cis-1,4-selectivity in the polymerization reaction may be decreased.

A reaction time is not particularly limited and may be in a range of 1 second to 10 days. The reaction time is appropriately selected depending on kinds of the monomer to be polymerized, kinds of the catalyst to be used, and conditions such as the reaction temperature.

According to the method of producing an addition polymer of the present invention, a polydiene having a high cis-1,4-content can be produced from a conjugate diene compound. For example, the polybutadiene produced by polymerizing butadiene according to the method of the present invention has a cis-1,4-content of 90% or more, preferably 95% or more, more preferably 98% or more, and still more preferably 99% or more. The cis-1,4-content can be determined from integral ratios of peaks in spectrum charts of $^1$H-NMR and $^{13}$C-NMR. Specific approach thereof is described in JP 2004-27179 A.

In addition, a number average molecular weight of the polybutadiene produced according to the method of the present invention is not particularly limited and generally about several hundreds of thousands to one million. Mw/Mn as an index of molecular weight distribution is preferably 3 or less and more preferably 2 or less. The average molecular weight and molecular weight distribution Mw/Mn can be determined using polystyrene as a standard substance by GPC.

According to the method of producing an addition polymer of the present invention, when polydiene is produced from a conjugate diene compound, the kind of the metallocene complex contained in the polymerization catalyst composition or the kind of the co-catalyst are appropriately selected, whereby a yield and cis-1,4-content of the polydiene to be obtained can be controlled. Specific procedure is as indicated by the above description for the polymerization catalyst composition.

EXAMPLES

Hereinafter, the present invention is described in more detail by way of examples, but the scope of the present invention is not limited by the examples. Note that $^1$H-NMR was measured using THF-d8 or 1,1,2,2-tetrachloroethane as a solvent at room temperature or 120° C. 13C-NMR was measured using 1,1,2,2-tetrachloroethane as a solvent at 120° C. X-ray crystallography was performed using RAXIS CS (Rigaku Corporation) or AFC-8 (Rigaku Corporation).

Synthesis of $(C_9H_7)_2GdN(SiMe_3)_2$

Figure 10:
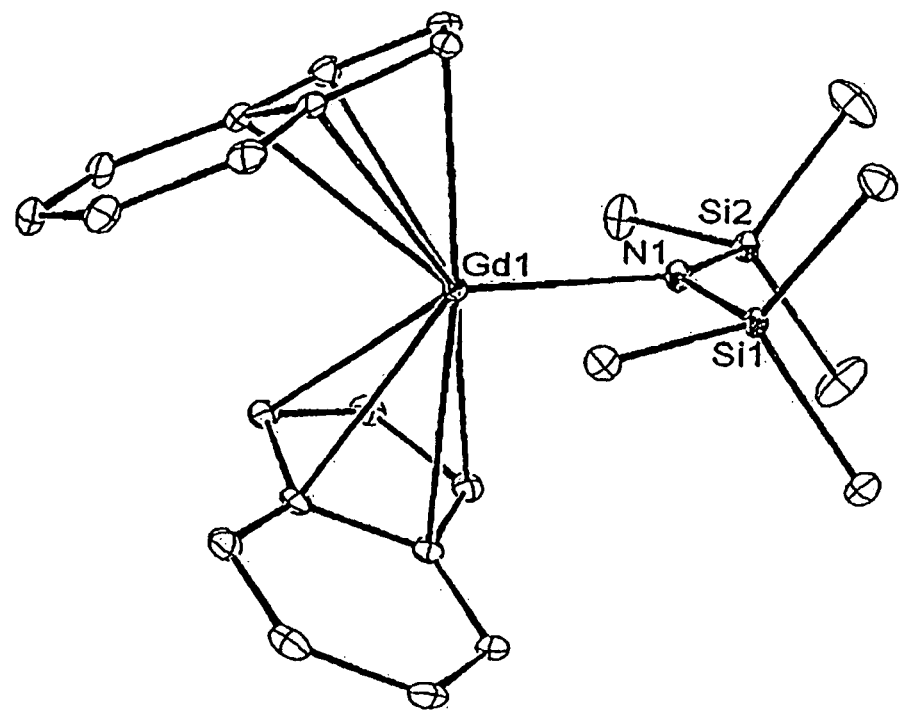
FIG. 10 is an ORTEP diagram showing a result of X-ray crystallography of $(C_9H_7)_2GdN(SiMe_3)_2$.

To 40 ml of a THF solution containing $GdCl_3$ (0.791 g, 3 mmol) manufactured by Strem Chemicals, Inc., 20 ml of a THF solution containing $C_9H_7Li$ (0.757 g, 6.2 mmol) synthesized from $C_9H_8$ (indene) available from SIGMA-ALDRICH Corp. and n-BuLi were dropped slowly under an atmosphere of nitrogen. Then, the mixture was stirred at 65° C. for 14 hours. After that, the THF was distilled off under reduced pressure and 50 ml of toluene were added instead of the THF. Then, 20 ml of a toluene solution containing $KN(SiMe_3)_2$ (0.519 g, 2.6 mmol) available from SIGMA-ALDRICH Corp. were dropped slowly to the mixture, followed by stirring at room temperature for 16 hours. After that, the toluene was distilled off under reduced pressure, 100 ml of hexane were added instead of the toluene, and a precipitate was filtered with a filter. After that, the hexane was distilled off under reduced pressure, whereby $(C_9H_7)_2GdN(SiMe_3)_2$ (0.724 g, 51%) as a yellowish white solid was obtained. For structural determination, the solid was recrystallized with toluene and the obtained monocrystal was subjected to X-ray crystallography (FIG. 10).

Figure 9:
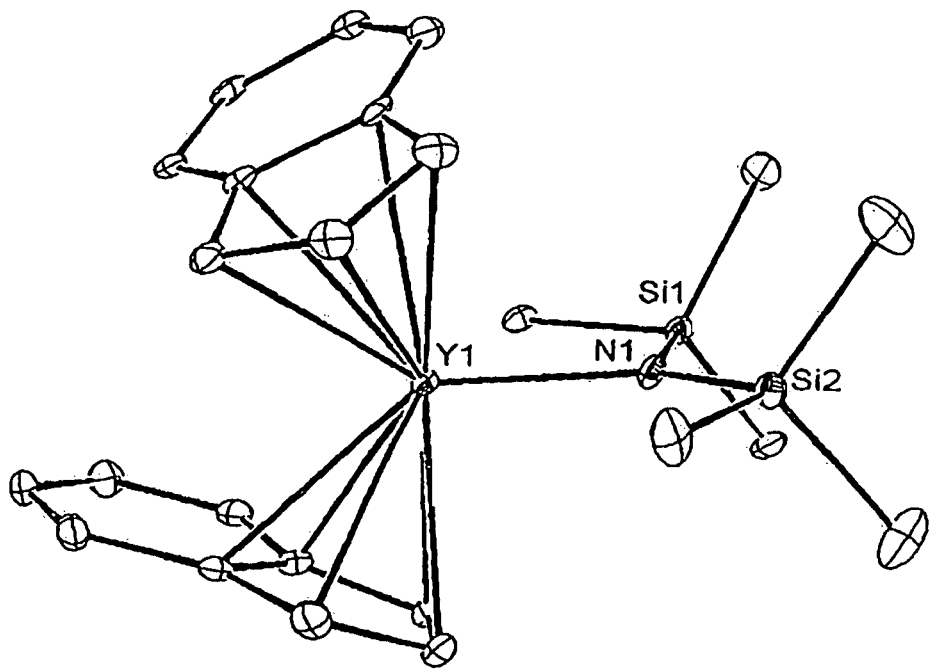
FIG. 9 is an ORTEP diagram showing a result of X-ray crystallography of $(C_9H_7)_2YN(SiMe_3)_2$.

In the same way, $(C_9H_7)_2ScN(SiMe_3)_2$ (50%) as an orange solid and $(C_9H_7)_2YN(SiMe_3)_2$ (42%) as a pink solid each were obtained (FIG. 9).

Figure 11:
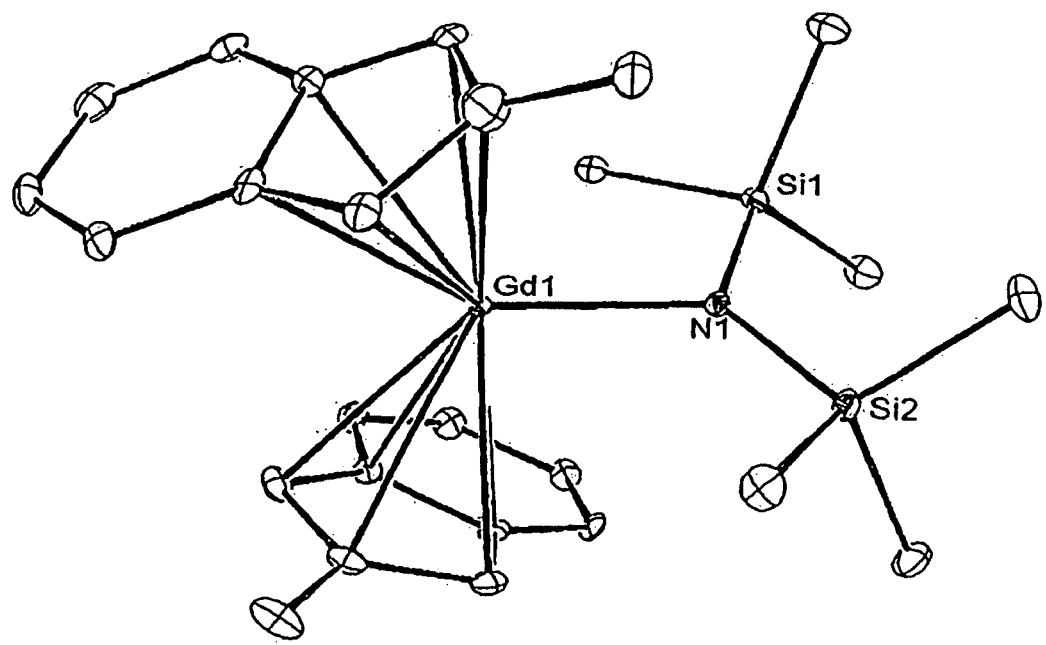
FIG. 11 is an ORTEP diagram showing a result of X-ray crystallography of $(2-MeC_9H_6)_2GdN(SiMe_3)_2$.

Synthesis of $(2\text{-}MeC_9H_6)_2GdN(SiMe_3)_2$ $(2\text{-}MeC_9H_6)_2GdN(SiMe_3)_2$ (0.988 g, 66%) as a yellow solid was obtained with the above method by using $2\text{-}MeC_9H_7$ (2-methyl indene) instead of $C_9H_8$ (indene). For structural determination, the solid was recrystallized with toluene, and the obtained monocrystal was subjected to X-ray crystallography (FIG. 11).

In the same way, $(2\text{-}MeC_9H_6)_2ScN(SiMe_3)_2$ (68%) as a yellow solid (FIG. 8), $(2\text{-}MeC_9H_6)_2YN(SiMe_3)_2$ (66%) as a white solid, $(2\text{-}MeC_9H_6)_2CeN(SiMe_3)_2$ (53%) as a pink solid, $(2\text{-}MeC_9H_6)_2PrN(SiMe_3)_2$ (76%) as a yellow solid, $(2\text{-}MeC_9H_6)_2NdN(SiMe_3)_2$ (51%) as a green solid (FIG. 4), $(2\text{-}MeC_9H_6)_2SmN(SiMe_3)_2$ (45%) as a red solid, and $(2\text{-}MeC_9H_6)_2HoN(SiMe_3)_2$ (46%) as an orange solid (FIG. 7) each were obtained.

Synthesis of $(2\text{-}PhC_9H_6)_2GdN(SiMe_3)_2$

Figure 6:
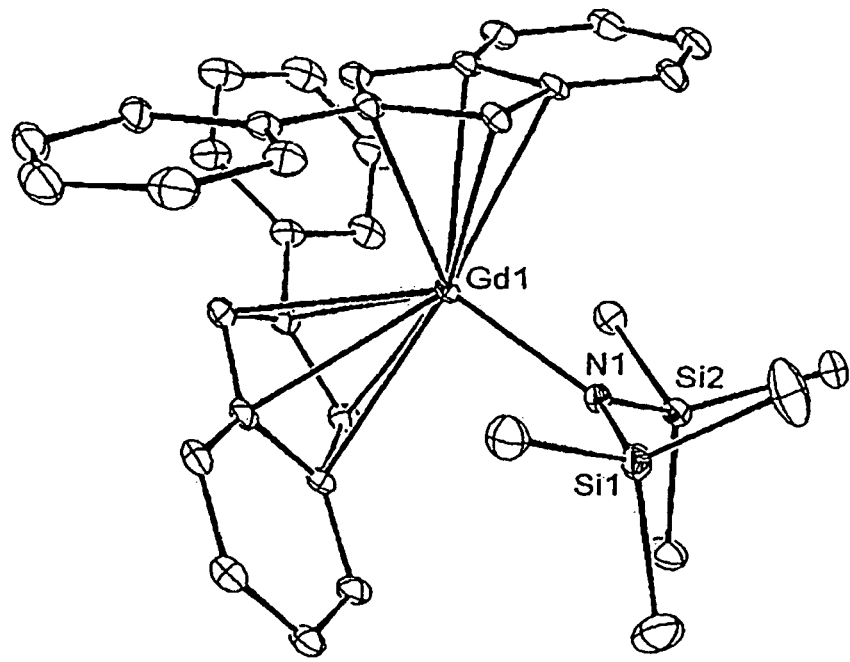
FIG. 6 is an ORTEP diagram showing a result of X-ray crystallography of $(2-PhC_9H_6)_2GdN(SiMe_3)_2$.
Figure 7:
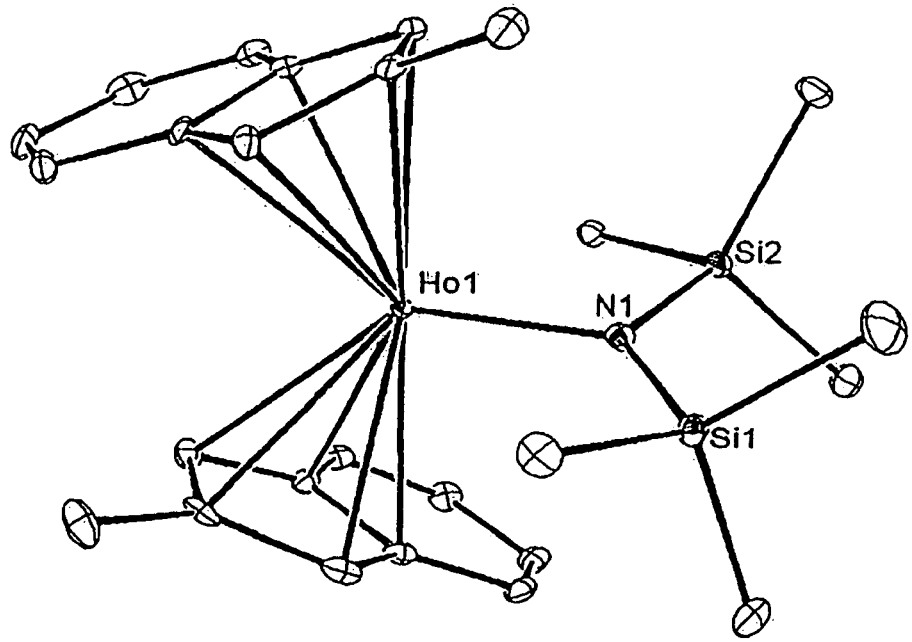
FIG. 7 is an ORTEP diagram showing a result of X-ray crystallography of $(2-MeC_9H_6)_2HoN(SiMe_3)_2$.
Figure 8:
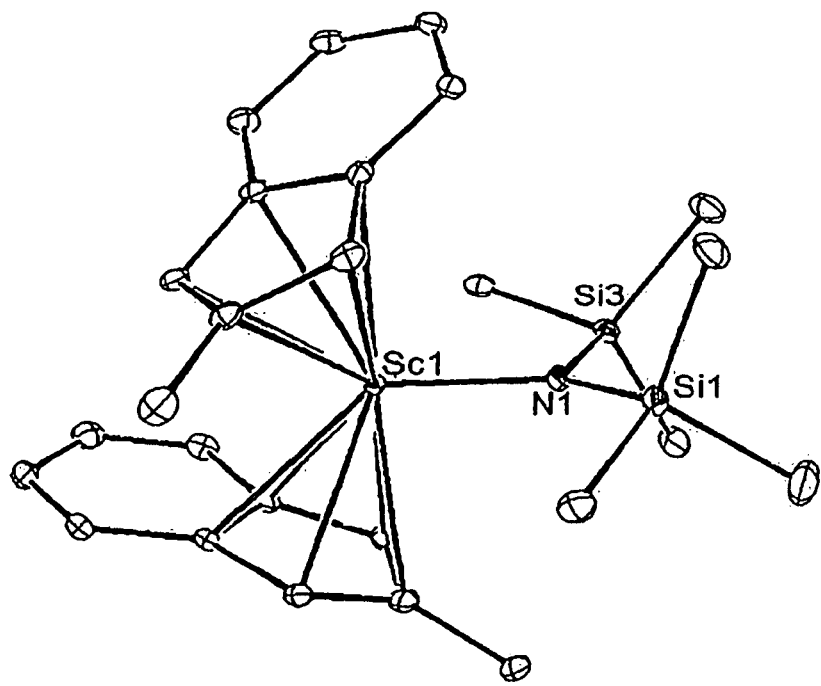
FIG. 8 is an ORTEP diagram showing a result of X-ray crystallography of $(2-MeC_9H_6)_2ScN(SiMe_3)_2$.

To 40 ml of a THF solution containing $GdCl_3$ (0.791 g, 3 mmol) manufactured by Strem Chemicals, Inc., 30 ml of a THF solution containing $2\text{-}PhC_9H_6Li$ (1.34 g, 6.2 mmol) synthesized from $2\text{-}PhC_9H_7$ (2-phenyl indene) available from SIGMA-ALDRICH Corp. and n-BuLi were dropped slowly under an atmosphere of nitrogen. Then, the mixture was stirred at room temperature for 48 hours, and further stirred at 65° C. for 14 hours. After that, the THF was distilled off under reduced pressure and 50 ml of toluene were added instead of the THF. Then, 20 ml of a toluene solution containing $KN(SiMe_3)_2$ (0.519 g, 2.6 mmol) available from SIGMA-ALDRICH Corp. were dropped slowly to the mixture, followed by stirring at room temperature for 16 hours. After that, the toluene was distilled off under reduced pressure, 100 ml of hexane were added instead of the toluene, and a precipitate was filtered with a filter. After that, the hexane was distilled off under reduced pressure, whereby $(2\text{-}PhC_9H_6)_2GdN(SiMe_3)_2$ (491 mg, 27%) as a yellow solid was obtained. For structural determination, the solid was recrystallized with toluene, and the obtained monocrystal was subjected to X-ray crystallography (FIG. 6).

Synthesis of $(2\text{-}MeC_9H_6)_2GdSi(SiMe_3)_3(THF)$

Figure 13:
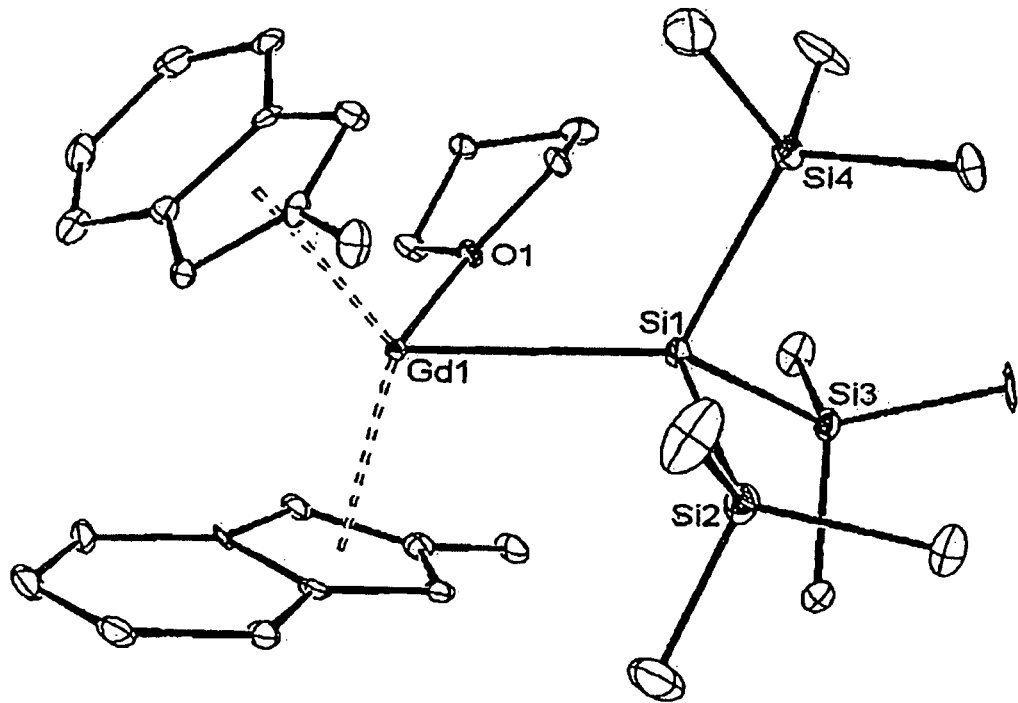
FIG. 13 is an ORTEP diagram showing a result of X-ray crystallography of $(2-MeC_9H_6)_2GdSi(SiMe_3)_3$.

To 20 ml of a THF solution containing $GdCl_3$ (0.264 g, 1 mmol), 20 ml of a THF solution containing $2\text{-}MeC_9H_6Li$ (0.286 g, 2.1 mmol) were dropped slowly under an atmosphere of nitrogen. Then, the mixture was stirred at 65° C. for 14 hours. After that, the THF was distilled off under reduced pressure and 50 ml of toluene were added instead of the THF. Then, 20 ml of a toluene solution containing $KSi(SiMe_3)_3$ (0.258 g, 0.90 mmol) available from SIGMA-ALDRICH Corp. were dropped slowly to the mixture, followed by stirring at room temperature for 16 hours. After that, the toluene was distilled off under reduced pressure, 50 ml of hexane were added instead of the toluene, and a precipitate was filtered with a filter. After that, the hexane was distilled off under reduced pressure, whereby $(2\text{-}MeC_9H_6)_2GdSi(SiMe_3)_3(THF)$ (426 mg, 64%) as a yellow solid was obtained. For structural determination, the solid was recrystallized with toluene, and the obtained monocrystal was subjected to X-ray crystallography (FIG. 13).

Synthesis of $[(2\text{-}MeC_9H_6)ScN(SiMe_3)_2(THF)_2][B(C_6F_5)_4]$

Figure 5:
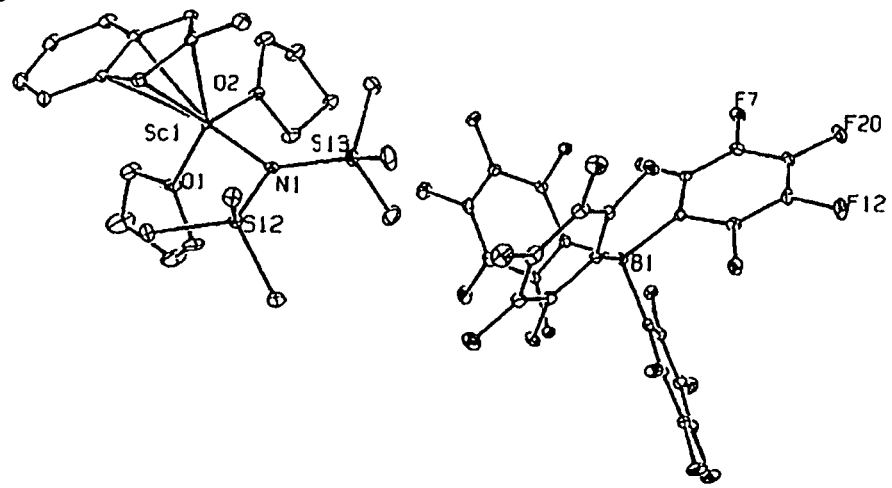
FIG. 5 is an ORTEP diagram showing a result of X-ray crystallography of $[(2-MeC_9H_6)ScN(SiMe_3)\ 2\ (THF)_2][B(C_6F_5)_4]$.

To 5 ml of a THF solution containing $(2\text{-}MeC_9H_6)_2ScN(SiMe_3)_2$ (0.145 g, 0.313 mmol), N,N-dimethylanilinium tetrakis(pentafluorophenyl)borate ($Me_2NHPhB(C_6F_5)_4$) (0.250 g, 0.312 mmol) was added under an atmosphere of nitrogen. Then, the mixture was stirred at room temperature for 30 minutes. After that, the THF was distilled off under reduced pressure and the obtained residual was washed with hexane three times. After that, the resultant was dissolved with 3 ml of THF, and a hexane layer was formed in the upper part thereof and left to stand, whereby a yellow precipitate generated. After the solvent was removed with a pipette gently, the resultant was dried slowly under reduced pressure, whereby [(2-$MeC_9H_6$)ScN($SiMe_3$)$_2$(THF)$_2$][B($C_6F_5$)$_4$] (190 mg, 53%) as a yellow crystal was obtained. The structure of the solid was confirmed by $^1$H-NMR (FIG. 1) and X-ray crystallography (FIG. 5).

Synthesis of [(2-$MeC_9H_6$)GdN($SiMe_3$)$_2$(THF)$_3$][B($C_6H_5$)$_4$]

Figure 12:
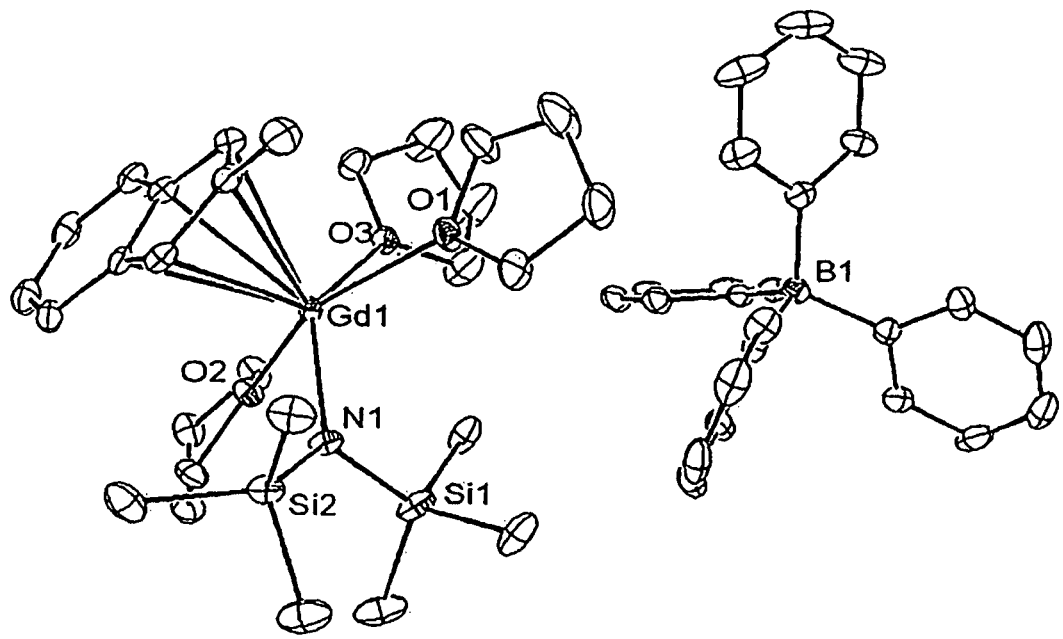
FIG. 12 is an ORTEP diagram showing a result of X-ray crystallography of $[(2-MeC_9H_6)GdN(SiMe_3)_2(THF)_2][B(C_6H_5)_4]$.

To 5 ml of a THF solution containing (2-$MeC_9H_6$)$_2$GdN($SiMe_3$)$_2$ (0.150 g, 0.260 mmol), triethylanilinium tetrakidphenyl borate ($Et_3$NHB ($C_6H_5$)$_4$) (0.110 g, 0.260 mmol) was added under an atmosphere of nitrogen. Then, the mixture was stirred at room temperature for 12 hours. After that, the THF was distilled off under reduced pressure and the obtained residual was washed with hexane three times to give an oil-like compound. After that, the residual was recrystallized with a THF/hexane mixed solvent, whereby [(2-$MeC_9H_6$)GdN($SiMe_3$)$_2$(THF)$_3$][B($C_6H_5$)$_4$] (150 mg, 59%) as a white crystal was obtained. The structure of the crystal was confirmed by X-ray crystallography (FIG. 12).

Synthesis of [($C_5Me_5$)$CH_2$($C_5Me_4$)GdN($SiMe_3$)$_2$(THF)$_2$][B($C_6F_5$)$_4$]

Figure 14:
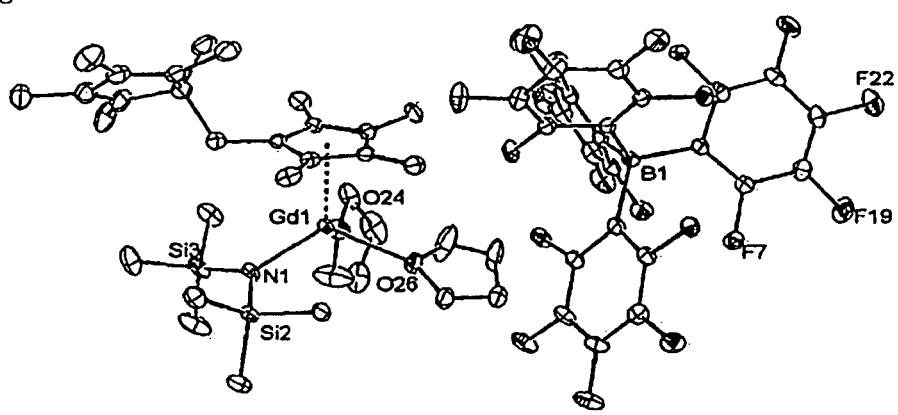
FIG. 14 is an ORTEP diagram showing a result of X-ray crystallography of $[(C_5Me_5)CH_2(C_5Me_4)GdN(SiMe_3)_2(THF)_2][B(C_6F_5)_4]$.

To 5 ml of a toluene solution containing ($C_5Me_5$)$_2$GdN($SiMe_3$)$_2$ (0.210 g, 0.357 mmol), triphenylcarbonium tetrakis(pentafluorophenyl)borate ($Ph_3CB(C_6F_5)_4$) (0.300 g, 0.325 mmol) was added under an atmosphere of nitrogen. Then, the mixture was stirred at room temperature for 30 minutes. After that, the toluene was distilled off under reduced pressure and the obtained residual was washed with hexane three times. After that, the resultant was dissolved with 3 ml of THF, and a hexane layer was formed in the upper part thereof and left to stand, whereby a yellow precipitate generated. After the solvent was removed with a pipette gently, the resultant was dried slowly under reduced pressure, whereby [($C_5Me_5$)$CH_2$($C_5Me_4$)GdN($SiMe_3$)$_2$(THF)$_2$][B($C_6F_5$)$_4$] (130 mg, 28%) as a colorless crystal was obtained. The structure of the crystal was confirmed by X-ray crystallography (FIG. 14).

Synthesis of Gd(N($SiHMe_2$)$_2$)$_3$(THF)$_2$

Figure 17:
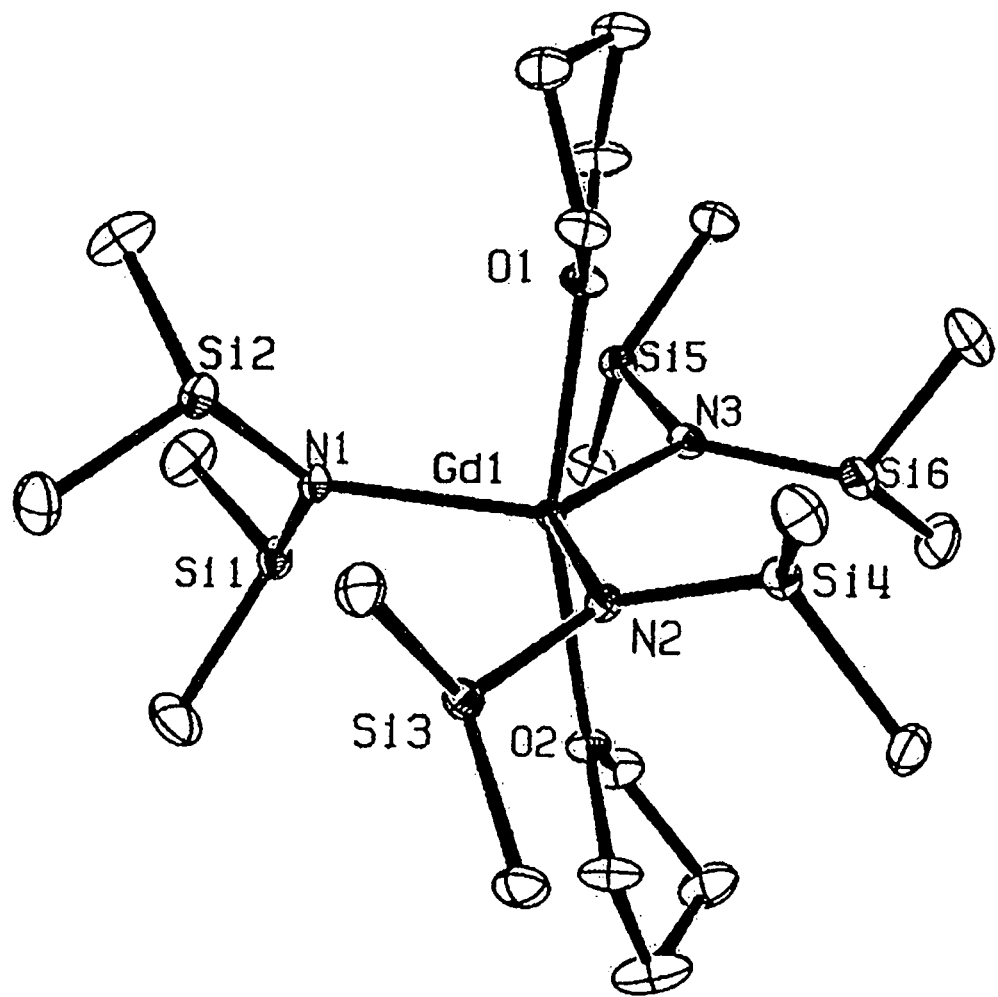
FIG. 17 is an ORTEP diagram showing a result of X-ray crystallography of $Gd(N(SiHMe_2)_2)_3(THF)_2$.

To 100 ml of a THF solution containing $GdCl_3$ (2.90 g, 11 mmol) manufactured by Strem Chemicals, Inc., 15 ml of an ether solution containing LiN($SiHMe_2$)$_2$ (4.18 g, 30 mmol) synthesized from nBuLi and NH ($SiHMe_2$)$_2$ were dropped slowly under an atmosphere of nitrogen. Then, the mixture was stirred at room temperature for 12 hours. After that, the solvent was distilled off under reduced pressure and 100 ml of hexane were added instead of the solvent. A precipitate was filtered with a filter. After that, the hexane was slowly distilled off under reduced pressure, whereby Gd(N($SiHMe_2$)$_2$)$_3$(THF)$_2$ (4.60 g, 66%) as a white crystal was obtained. For structural determination, the obtained monocrystal was subjected to X-ray crystallography (FIG. 17).

Synthesis of (2-$PhC_9H_6$)$_2$GdN($SiHMe_2$)$_2$

Gd(N($SiHMe_2$)$_2$)$_3$(THF)$_2$ (2.79 g, 4 mmol) and 2-$PhC_9H_7$ (2-phenyl indene) (1.50 g, 7.8 mmol) available from SIGMA-ALDRICH Corp. were dissolved in 60 ml of a toluene solution under an atmosphere of nitrogen, followed by stirring at 120° C. for 4 hours. After that, the toluene was distilled off under reduced pressure and 60 ml of toluene were added again, followed by stirring at 120° C. for 15 hours. Then, the toluene was distilled off under reduced pressure, and the residual was washed with hexane several times, whereby (2-$PhC_9H_6$)$_2$GdN($SiHMe_2$)$_2$ (1.92 g, 73%) as a yellow solid was obtained. In addition, an experiment was conducted with the same method except that Tb (N($SiHMe_2$) 2)$_3$ (THF) 2 was used instead of Gd(N($SiHMe_2$)$_2$)$_3$(THF)$_2$, whereby (2-$PhC_9H_6$)$_2$TbN($SiHMe_2$)$_2$ (1.85 g, 70%) was obtained.

Synthesis of (1-Me-2-$PhC_9H_6$)$_2$GdN($SiHMe_2$)$_2$ (1-Me-2-$PhC_9H_6$)$_2$GdN($SiHMe_2$)$_2$ (35%) as an orange solid was obtained with the same method as that of (2-$PhC_9H_6$)$_2$GdN($SiHMe_2$)$_2$ by using 1-Me-2-$PhC_9H_7$ (1-methyl-2-phenyl indene) synthesized by the method described in Organometallics, 1997, 16, 3635-3639 instead of 2-phenyl indene.

Synthesis of (i$PrC_5H_4$)$_2$GdN($SiMe_3$)$_2$

To 20 ml of a THF solution containing $GdCl_3$ (0.527 g, 2 mmol) manufactured by Strem Chemicals, Inc., 20 ml of a THF solution containing i$PrC_5H_4$Na (0.534 g, 4.1 mmol) available from SIGMA-ALDRICH Corp. were dropped slowly under an atmosphere of nitrogen. Then, the mixture was stirred at room temperature for 16 hours. After that, the THF was distilled off under reduced pressure and 30 ml of toluene were added instead of the THF. Then, 20 ml of a toluene solution containing K[N($SiMe$)$_3$]$_2$ (0.360 g, 1.8 mmol) available from SIGMA-ALDRICH Corp. were dropped slowly to the mixture, followed by stirring at room temperature for 16 hours. After that, the toluene was distilled off under reduced pressure, 100 ml of hexane were added instead of the toluene, and a precipitate was filtered with a filter. After that, the hexane was distilled off under reduced pressure, whereby (i$PrC_5H_4$)$_2$GdN($SiMe_3$)$_2$ (0.805 g, 84%) as a yellow liquid was obtained.

Example 1

0.03 mmol of bis(indenyl)gadolinium bis(trimethylsilylamide) [($C_9H_7$)$_2$GdN($SiMe_3$) 2] was loaded into a sufficiently-dried 30-ml pressure resistant glass bottle in a glove box under an atmosphere of nitrogen and dissolved with 18 mL of toluene. Next, 0.15 mmol of triisobutyl aluminum and 0.03 mmol of N,N-dimethylanilinium tetrakis(pentafluorophenyl) borate ($Me_2NHPhB(C_6F_5)_4$) were added into the bottle, and the bottle was capped. The bottle was taken from the glove box and 0.54 g of 1,3-butadiene was loaded into the bottle, followed by polymerization at 20° C. for 15 minutes. After the polymerization, 10 ml of a methanol solution containing 10 wt % 2,6-bis(t-butyl)-4-methylphenol (BHT) were added to stop the reaction. Further, the polymer was separated with a large amount of a mixture solvent of methanol and hydrochloric acid and dried at 60° C. in vacuum. A yield of the obtained polymer was 93 wt %. A microstructure of the polymer had a cis-content of 98.9 mol %, a number average molecular weight of 120,000, and Mw/Mn of 1.26.

Example 2

A polymerization was performed with the same method as in Example 1 except that bis(2-methylindenyl) gadoliniumbis(trimethylsilylamide) [(2-$MeC_9H_6$)$_2$GdN($SiMe_3$)$_2$] was used instead of bis(indenyl)gadolinium bis(trimethylsilylamide). A yield of the obtained polymer was 98 wt %. A microstructure of the polymer had a cis-content of 99.0 mol %, a number average molecular weight of 110,000, and Mw/Mn of 1.12.

Example 3

A polymerization was performed with the same method as in Example 1 except that bis(2-phenyl indenyl) gadoliniumbis (trimethylsilylamide) [(2-PhC$_9$H$_6$)$_2$GdN(SiMe$_3$)$_2$] was used instead of bis(indenyl)gadolinium bis(trimethylsilylamide). A yield of the obtained polymer was 93 wt %. A microstructure of the polymer had a cis-content of 99.0 mol %, a number average molecular weight of 220,000, and Mw/Mn of 1.46.

Example 4

A polymerization was performed with the same method as in Example 3 except that triphenylcarbonium tetrakis(pentafluorophenyl)borate (Ph$_3$CB(C$_6$F$_5$)$_4$) was used instead of N,N-dimethylanilinium tetrakis(pentafluorophenyl)borate. A yield of the obtained polymer was 98 wt %. A microstructure of the polymer had a cis-content of 99.3 mol %, a number average molecular weight of 130,000, and Mw/Mn of 1.19.

Example 5

5 mmol of bis(indenyl)gadolinium bis(trimethylsilylamide) [(C$_9$H$_7$)$_2$GdN(SiMe$_3$)$_2$] was loaded into a sufficiently-dried 1-L pressure resistant glass bottle in a glove box under an atmosphere of nitrogen and dissolved with 1 mL of toluene. Next, MMAO (a toluene-soluble aluminoxane available from Tosoh Finechem Corporation) in such an amount that an element ratio of Al to Gd was 150 was added, and then, 1 mmol of triisobutyl aluminum was added into the bottle, and the bottle was capped. The bottle was taken from the glove box and 125 mL of dehydrated toluene was added in the bottle. After that, 27 g of 1,3-butadiene were loaded under low temperature, followed by polymerization at 50° C. for 2 hours. After the polymerization, 50 ml of a methanol solution containing 10 wt % 2,6-bis(t-butyl)-4-methylphenol (BHT) were added to stop the reaction. Further, the polymer was separated with a large amount of a mixture solvent of methanol and hydrochloric acid and dried at 60° C. in vacuum. A yield of the obtained polymer was 48 wt %. A microstructure of the polymer had a cis-content of 98.7 mol %, a number average molecular weight of 290,000, and Mw/Mn of 1.85.

Example 6

A polymerization was performed with the same method as in Example 5 except that bis(2-methylindenyl)gadoliniumbis (trimethylsilylamide) [(2-MeC$_9$H$_6$)$_2$GdN(SiMe$_3$)$_2$] instead of bis(indenyl)gadolinium bis(trimethylsilylamide) and 1.5 mmol of triisobutyl aluminum were used, and the polymerization was performed for 30 minutes. A yield of the obtained polymer was 90 wt %. A microstructure of the polymer had a cis-content of 98.2 mol %, a number average molecular weight of 260,000, and Mw/Mn of 1.75.

Example 7

A polymerization was performed with the same method as in Example 5 except that bi(2-phenyl indenyl) gadoliniumbis (trimethylsilylamide) [(2-PhC$_9$H$_6$)$_2$GdN(SiMe$_3$) 2] instead of bis(indenyl)gadolinium bis(trimethylsilylamide), MMAO in such an amount that an element ratio of Al to Gd was 300, and 2.5 mmol of triisobutyl aluminum were used, and the polymerization was performed for 30 minutes. A yield of the obtained polymer was 94 wt %. A microstructure of the polymer had a cis-content of 98.8 mol %, a number average molecular weight of 310,000, and Mw/Mn of 1.88.

Example 8

Figure 2:
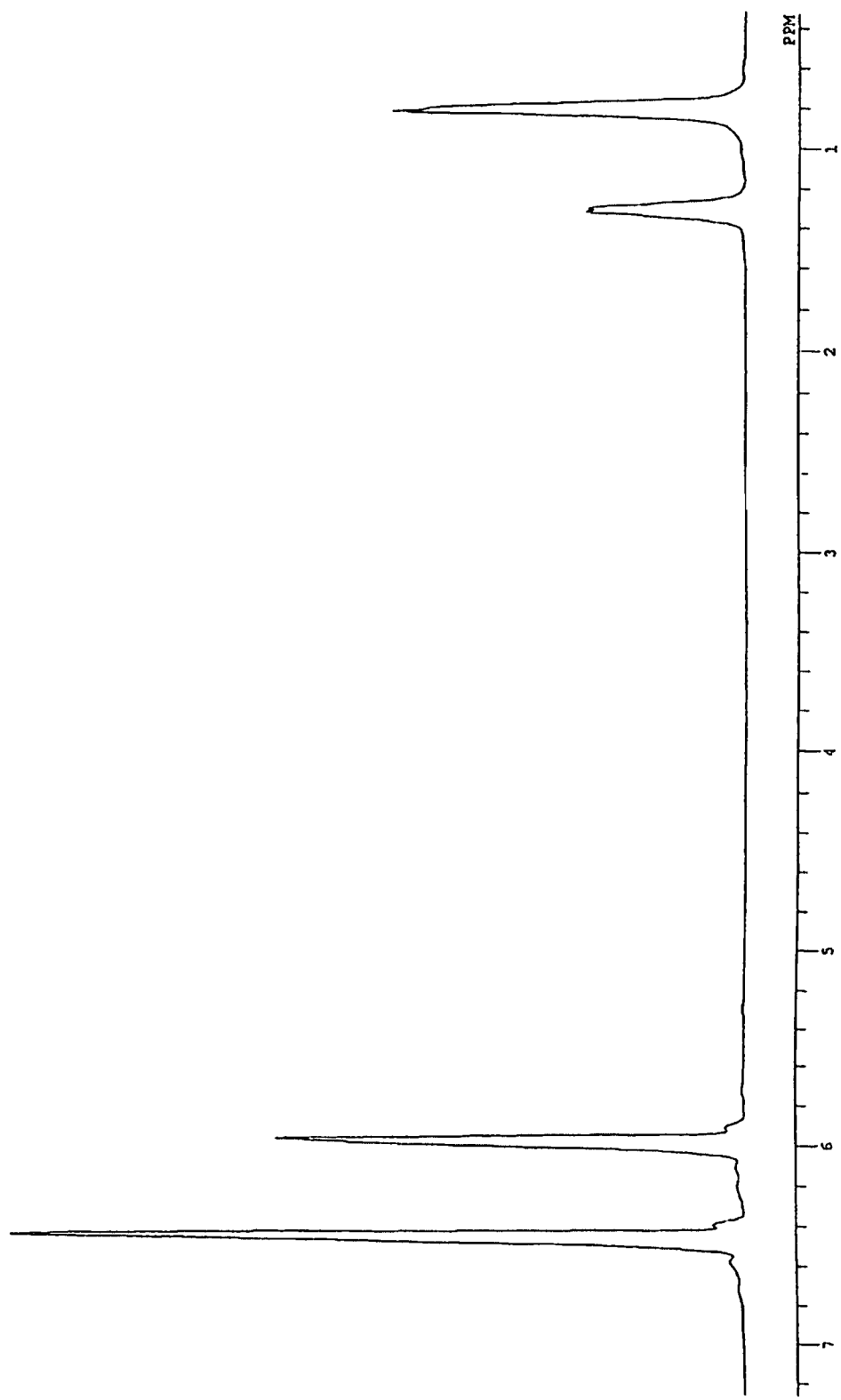
FIG. 2 is an $^1$H-NMR spectrum chart of a syndiotactic polystyrene obtained in Example 8.
Figure 3:
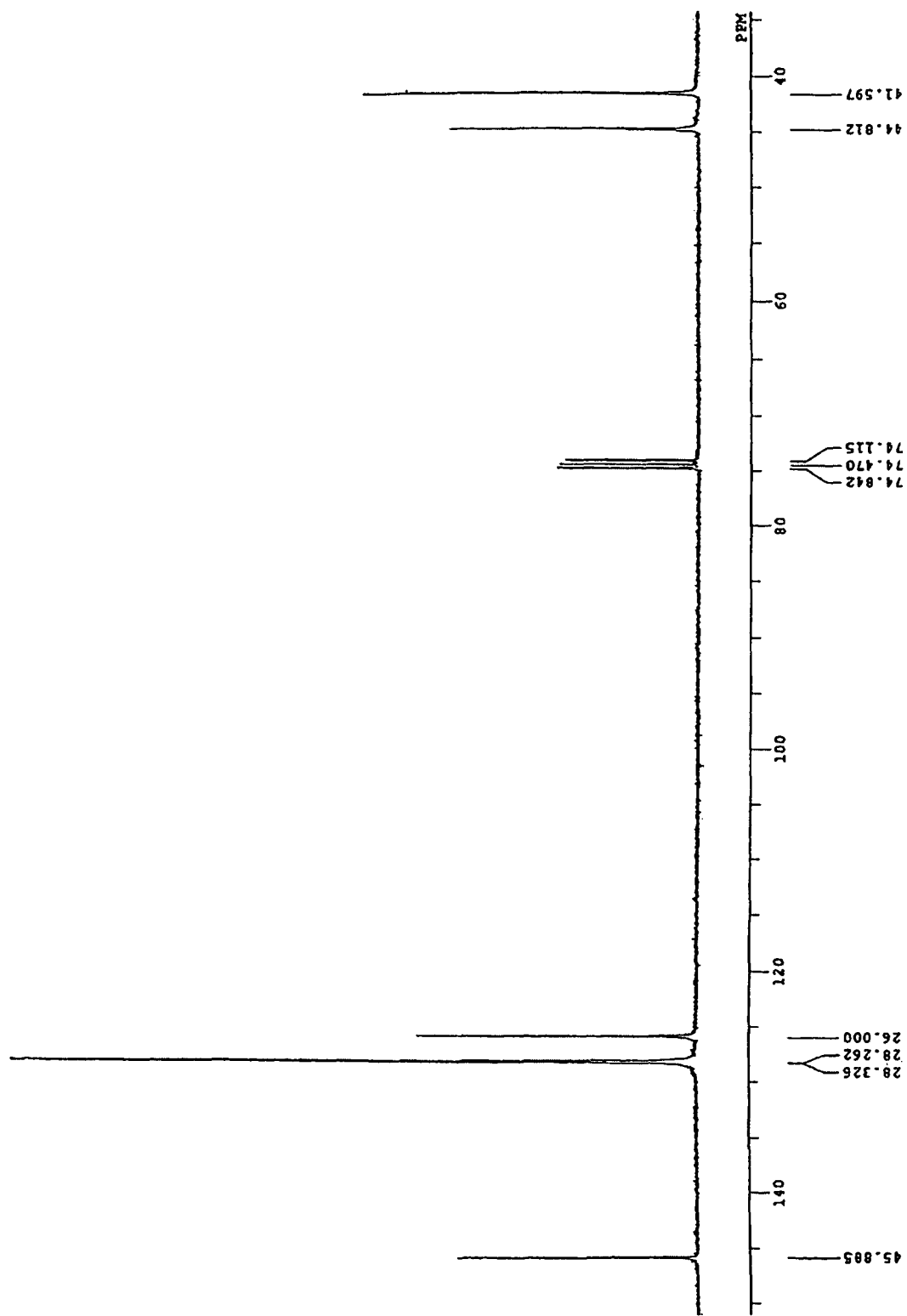
FIG. 3 is a $^{13}$C-NMR spectrum chart of the syndiotactic polystyrene obtained in Example 8.
Figure 4:
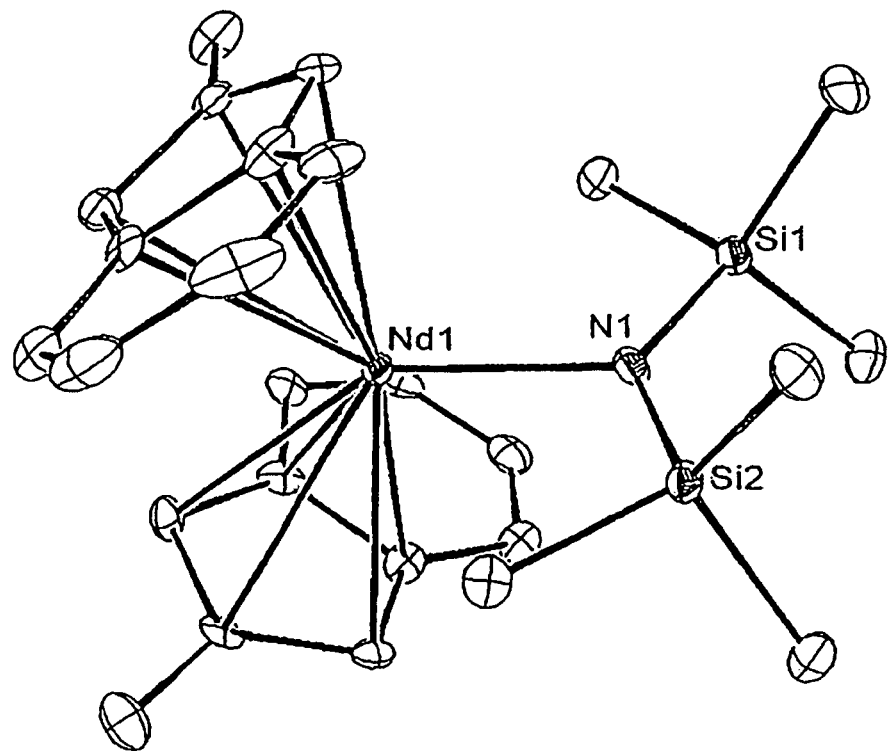
FIG. 4 is an ORTEP diagram showing a result of X-ray crystallography of $(2-MeC_9H_6)_2NdN(SiMe_3)_2$.

0.02 mmol of bis(indenyl)scandium bis(trimethylsilylamide) [(C$_9$H$_7$)$_2$ScN(SiMe$_3$)$_2$] was loaded into a sufficiently-dried 20-mL glass container in a glove box under an atmosphere of nitrogen, and dissolved with 10 mL of toluene. Next, 0.1 mmol of triisobutyl aluminum and 0.02 mmol of N,N-dimethylanilinium tetrakis(pentafluorophenyl)borate (Me$_2$NHPhB(C$_6$F$_5$)$_4$) were added to the container. After that, 2.15 g of styrene were loaded, followed by polymerization at room temperature for 5 minutes. After the polymerization, a polymer was separated with a large amount of a mixture solvent of methanol and hydrochloric acid and dried at 60° C. in vacuum. A yield of the obtained polymer was 50 wt %. The obtained polymer was not dissolved at all in solvent media such as toluene, cyclohexane, THF, and chloroform, but was dissolved in 1,1,2,2-tetrachloroethane or dichlorobenzene by heating. By $^1$H-NMR (FIG. 2), $^{13}$C-NMR spectrum (FIG. 3), and DSC measurement (Tm=257° C.), the polymer was confirmed to be a syndiotactic polystyrene.

Example 9

A polymerization was performed with the same method as in Example 8 except that bis(2-methylindenyl) scandium bis (trimethylsilylamide) [(2-MeC$_9$H$_6$)$_2$ScN(SiMe$_3$)$_2$] was used instead of bis(indenyl)scandium bis(trimethylsilylamide). A yield of the obtained polymer was 100 wt %, and physical properties of the obtained polymer were the same as those of Example 8.

Example 10

Figure 15:
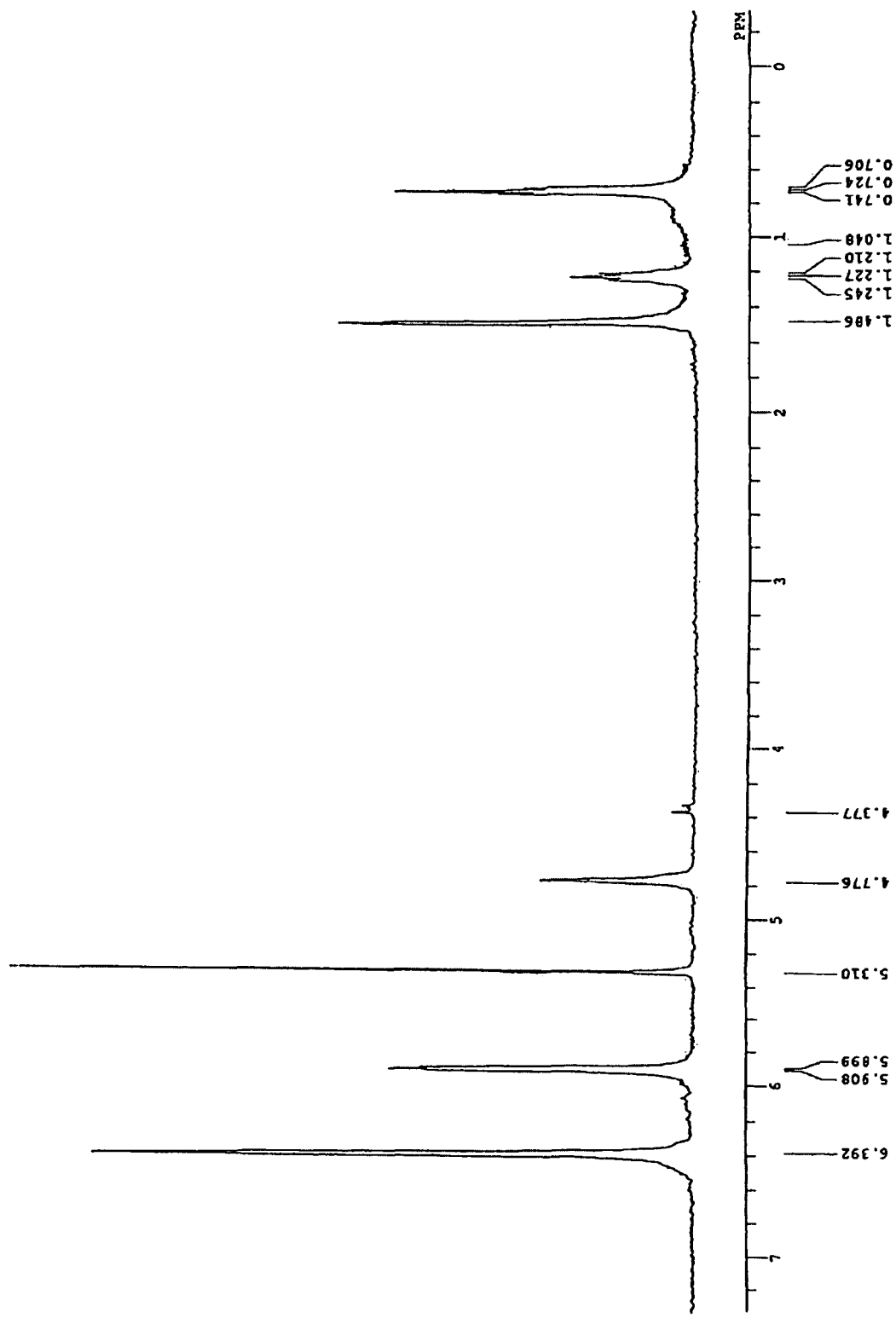
FIG. 15 is an $^1$H-NMR spectrum chart of a styrene-butadiene copolymer obtained in Example 10.

0.03 mmol of bis(2-methylindenyl)scandium bis(trimethylsilylamide) [(2-MeC$_9$H$_6$)$_2$ScN(SiMe$_3$) 2] was loaded into a sufficiently-dried 5-mL glass container in a glove box under an atmosphere of nitrogen and dissolved with 1.5 mL of toluene. Next, 0.15 mmol of triisobutyl aluminum and 0.03 mmol of N,N-dimethylanilinium tetrakis(pentafluorophenyl) borate (Me$_2$NHPhB(C$_6$F$_5$)$_4$) were added to the bottle to prepare a catalyst solution. Then, the bottle was sealed and taken from the glove box. 5 ml of toluene, 2.34 g of styrene, 0.41 g of 1,3-butadiene were loaded into a 30-ml pressure resistant glass bottle and the bottle was capped to prepare a monomer solution. The catalyst solution was added to the monomer solution with an injection syringe, followed by polymerization at room temperature for 30 minutes. After the polymerization, the polymer was separated with a large amount of a mixture solvent of methanol and hydrochloric acid and dried at 60° C. in vacuum. A yield of the obtained polymer was 100 wt %. The obtained polymer was not dissolved at all in solvent media such as toluene, cyclohexane, THF, and chloroform, but was dissolved in 1,1,2,2-tetrachloroethane or dichlorobenzene by heating. By $^1$H-NMR measurement (FIG. 15), the polymer was confirmed to be a copolymer having 75 mol % of a syndiotactic polystyrene part and 25 mol % of a polybutadiene part.

Example 11

Figure 16:
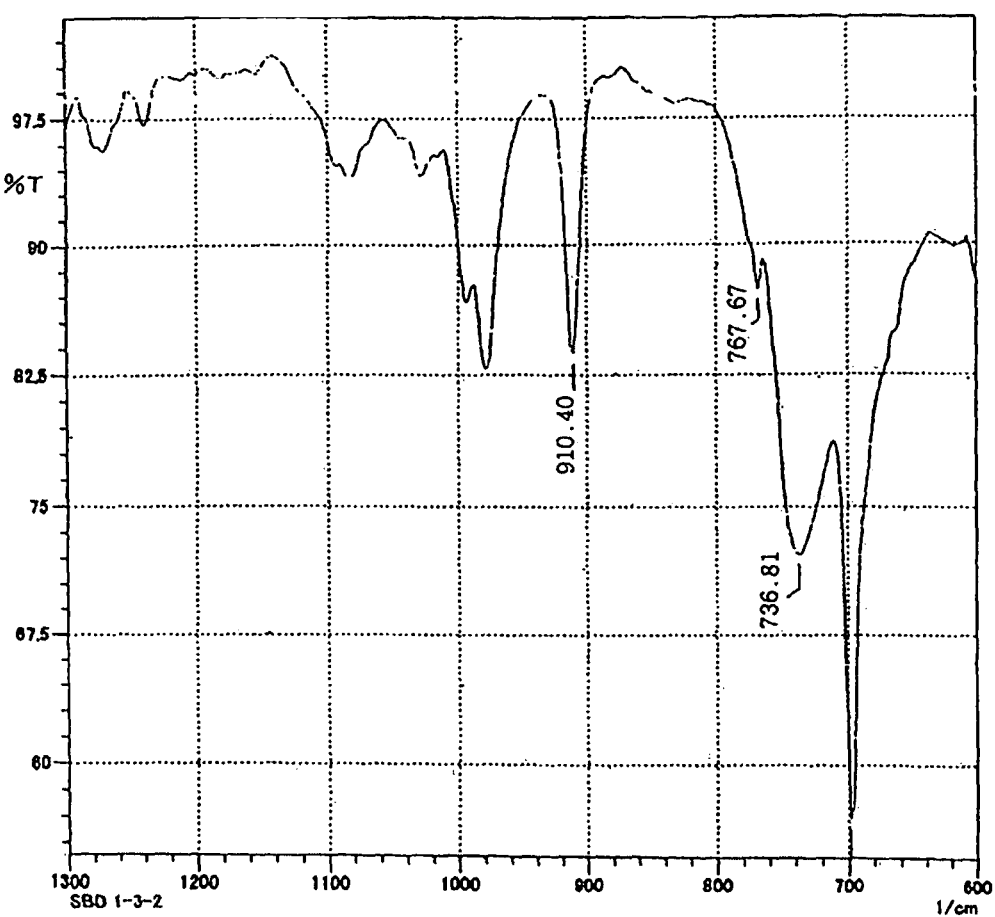
FIG. 16 is an IR spectrum chart of a styrene-butadiene copolymer obtained in Example 11.

A polymerization was performed with the same method as in Example 10 except that 0.78 g of styrene and 1.35 g of 1,3-butadiene were loaded. A yield of the obtained polymer was 80 wt %. The obtained polymer was not dissolved at all in solvent media such as toluene, cyclohexane, THF, and chloroform, but was dissolved in 1,1,2,2-tetrachloroethane or dichlorobenzene by heating. By $^1$H-NMR and IR measurement (FIG. 16), the polymer was confirmed to be a copolymer having 20 mol % of a syndiotactic polystyrene part and 80 mol % of a butadiene part containing high cis-content.

Example 12

0.03 mmol of bis(indenyl)scandium bis(trimethylsilylamide) [(C$_9$H$_7$)$_2$ScN(SiMe$_3$)$_2$] was loaded into a sufficiently-dried 100-mL pressure resistant glass container in a glove box under an atmosphere of nitrogen and dissolved with 30 mL of toluene. Next, 0.15 mmol of triisobutyl aluminum and 0.03 mmol of N,N-dimethylanilinium tetrakis(pentafluorophenyl) borate (Me$_2$NHPhB (C$_6$F$_5$)$_4$) were added into the container. After that, ethylene was polymerized at 1 atm and room temperature for 15 minutes. After the polymerization, the polymer was separated with a large amount of a mixture solvent of methanol and hydrochloric acid and dried at 60° C. in vacuum. A yield of the obtained polymer was 500 mg. The obtained polymer was not dissolved at all in solvent media such as toluene, cyclohexane, THF, and chloroform.

Example 13

1.5 mmol of bis(2-phenyl indenyl)gadolinium bis(dimethylsilylamide) [(2-PhC$_9$H$_6$)$_2$GdN(SiHMe$_2$)$_2$] were loaded into a sufficiently-dried 1-L pressure resistant glass bottle in a glove box under an atmosphere of nitrogen. Next, TMAO-211 (a toluene-soluble aluminoxane available from Tosoh Finechem Corporation) in such an amount that an element ratio of Al to Nd was 300, and 7.5 mmol of triisobutyl aluminum were added into the bottle and the bottle was capped. After that, the bottle was taken from the glove box, and 486 g of dehydrated toluene were added into the bottle. After that, 81 g of 1,3-butadiene were loaded into the bottle under low temperatures, followed by polymerization at 70° C. for 90 minutes. After the polymerization, 50 ml of a methanol solution containing 10 wt % 2,6-bis(t-butyl)-4-methylphenol (BHT) were added to stop the reaction. Further, the polymer was separated with a large amount of a mixture solvent of methanol and hydrochloric acid and dried at 60° C. in vacuum. A yield of the obtained polymer was 78 wt %. A microstructure of the polymer had a cis-content of 99.0 mol %, a number average molecular weight of 270,000, and Mw/Mn of 1.94.

Example 14

1.5 mmol of bis(2-phenyl indenyl)gadolinium bis(dimethylsilylamide) [(2-PhC$_9$H$_6$)$_2$GdN(SiHMe$_2$) 2] were loaded into a sufficiently-dried 1-L pressure resistant glass bottle in a glove box under an atmosphere of nitrogen. Next, TMAO-341 (a hexane-soluble aluminoxane available from Tosoh Finechem Corporation) in such an amount that an element ratio of Al to Nd was 2,600, and 15 mmol of triisobutyl aluminum were added into the bottle and the bottle was capped. After that, the bottle was taken from the glove box, and 486 g of dehydrated cyclohexane were added into the bottle. After that, 81 g of 1,3-butadiene were loaded into the bottle under low temperatures, followed by polymerization at 70° C. for 90 minutes. After the polymerization, 50 ml of a methanol solution containing 10 wt % 2,6-bis(t-butyl)-4-methylphenol (BHT) were added to stop the reaction. Further, the polymer was separated with a large amount of a mixture solvent of methanol and hydrochloric acid and dried at 60° C. in vacuum. A yield of the obtained polymer was 50 wt %. A microstructure of the polymer had a cis-content of 98.8 mol %, a number average molecular weight of 320,000, and Mw/Mn of 2.12.

Example 15

1.5 mmol of bis(1-methyl-2-phenyl indenyl)gadolinium bis(dimethylsilylamide) [(1-Me-2-PhC$_9$H$_5$)$_2$GdN(SiHMe$_2$) 2] were loaded into a sufficiently-dried 1-L pressure resistant glass bottle in a glove box under an atmosphere of nitrogen. Next, TMAO-211 (a toluene-soluble aluminoxane available from Tosoh Finechem Corporation) in such an amount that an element ratio of Al to Nd was 300, and 6 mmol of triisobutyl aluminum were further added into the bottle and the bottle was capped. After that, the bottle was taken from the glove box, and 486 g of dehydrated toluene were added to the bottle. After that, 81 g of 1,3-butadiene were loaded into the bottle under low temperatures, followed by polymerization at 70° C. for 90 minutes. After the polymerization, 50 ml of a methanol solution containing 10 wt % 2,6-bis(t-butyl)-4-methylphenol (BHT) were added to stop the reaction. Further, the polymer was separated with a large amount of a mixture solvent of methanol and hydrochloric acid and dried at 60° C. in vacuum. A yield of the obtained polymer was 80 wt %. A microstructure of the polymer had a cis-content of 98.8 mol %, a number average molecular weight of 330,000, and Mw/Mn of 1.79.

Industrial Applicability

The metallocene complex and the half metallocene cation complex of the present invention may be used as a polymerization catalyst, for example, and hence provides a novel polymerization reaction for a conjugate diene, a monoolefin, and the like. According to the synthetic method for a half metallocene cation complex of the present invention, a catalyst having high polymerization reactivity can be easily produced at low cost. By using the metallocene complex of the present invention as the polymerization catalyst for a conjugate diene, a diene polymer having a high cis 1,4-content in its microstructure can be produced at high yields. By using the half metallocene cation complex of the present invention as a polymerization catalyst for a styrene, a styrene polymer having high syndiotacticity in the conformation can be produced at high yields.

The invention claimed is:

1. A metallocene complex represented by the following general formula (I),

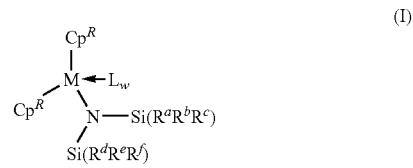

where: M represents samarium, neodymium, praseodymium, gadolinium, terbium, cerium, holmium, scandium, or yttrium;

Cp$^R$ independently represents an unsubstituted or substituted indenyl group, and is represented by the formula C$_9$H$_{7-x}$R$_x$ wherein x represents an integer of 0 to 7 or is represented by the formula C$_9$H$_{11-x}$R$_x$ wherein x represents an integer of 0 to 11, and R independently represents a hydrocarbyl group or a trimethyl silyl group;

R$^a$ to R$^f$ independently represents hydrogen or an alkyl group having 1 to 3 carbon atoms;

L represents a neutral Lewis base; and w represents an integer of 0 to 3.

2. A polymerization catalyst composition, comprising (i) the metallocene complex according to claim 1 and (ii) a co-catalyst.

3. The polymerization catalyst composition according to claim 2, which is used for polymerizing a conjugate diene.

4. The polymerization catalyst composition according to claim 2, further comprising an aluminoxane.

5. The polymerization catalyst composition according to claim 2, further comprising one of or both of an organic aluminum compound and an ionic compound.

6. A method of producing an addition polymer, comprising polymerizing addition-polymerizable monomers in the presence of the polymerization catalyst composition according to claim 2.

7. The method according to claim 6, wherein:
the addition-polymerizable monomer is a conjugate diene; and the addition polymer is a conjugate diene polymer.

8. The method according to claim 6, wherein:
the addition-polymerizable monomer is 1,3-butadiene; and the addition polymer is a butadiene polymer.

9. The method according to claim 6, wherein:
the addition-polymerizable monomer is a disconjugate olefin; and the addition polymer is a disconjugate olefin polymer.

10. The method according to claim 6, wherein:
the addition-polymerizable monomer is at least one monoolefin selected from C2 to C10 disconjugate olefins and a styrene; and the addition polymer is a monoolefin polymer or copolymer each obtained by reacting at least one selected from C2 to C10 disconjugate olefins with styrene.

11. The method according to claim 10, wherein:
the addition-polymerizable monomer further comprises a conjugate diene; and
the addition polymer is a copolymer of the conjugate diene and the monoolefin.

12. A method for producing a half metallocene cation complex represented by the following general formula (III), comprising subjecting a compound represented by the following general formula (IV) to a reaction with an ionic compound represented by the general formula $[A]^+[B]^-$

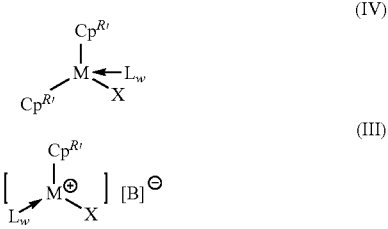

where: M represents a lanthanoid element, scandium, or yttrium;
$Cp^{R'}$ independently represents an unsubstituted or substituted cyclopentadienyl, indenyl, or fluorenyl group;
X represents a hydrogen atom, a halogen atom, an alkoxide group, a thiolate group, an amide group, a silyl group, or a hydrocarbon group having 1 to 20 carbon atoms;
L represents a neutral Lewis base;
w represents an integer of 0 to 3;
$[A]^+$ represents a cation; and
$[B]^-$ represents a non-coordinating anion.

13. The method according to claim 12, wherein $Cp^{R'}$ represents an unsubstituted or substituted indenyl group.

14. The metallocene complex according to claim 1, wherein R independently represents a methyl group, an ethyl group, a phenyl group, a benzyl group or a trimethyl silyl group.

* * * * *